(12) United States Patent
Pitterna et al.

(10) Patent No.: US 7,521,429 B2
(45) Date of Patent: Apr. 21, 2009

(54) AVERMECTIN B1 MONOSACCHARIDE DERIVATIVES

(75) Inventors: Thomas Pitterna, Basel (CH); Pierre Jung, Basal (CH); Fiona Murphy Kessabi, Basel (CH); Jerome Cassayre, Basel (CH); Laura Quaranta, Basel (CH); Ottmar Franz Hueter, Basel (CH)

(73) Assignee: Merial Limited, Duluth, GA (US)

( * ) Notice: Subject to any disclaimer, the term of this patent is extended or adjusted under 35 U.S.C. 154(b) by 0 days.

(21) Appl. No.: 10/560,390

(22) PCT Filed: Jun. 15, 2004

(86) PCT No.: PCT/EP2004/006442

§ 371 (c)(1),
(2), (4) Date: Mar. 22, 2006

(87) PCT Pub. No.: WO2004/111070

PCT Pub. Date: Dec. 23, 2004

(65) Prior Publication Data

US 2006/0229263 A1   Oct. 12, 2006

(30) Foreign Application Priority Data

Jun. 16, 2003 (GB) ................... 0313937.5

(51) Int. Cl.
*A61K 31/70* (2006.01)
*C07H 17/08* (2006.01)
(52) U.S. Cl. .......................... 514/30; 536/7.1
(58) Field of Classification Search ............ 536/7.1; 514/30
See application file for complete search history.

(56) References Cited

U.S. PATENT DOCUMENTS 4,622,313 A    11/1986   Wyvratt, Jr.
5,208,222 A *  5/1993   Meinke et al. ............... 514/30
6,933,260 B2   8/2005   Cassayre

FOREIGN PATENT DOCUMENTS

EP    0 506 331 A     9/1992
WO    WO 03/053988 A  7/2003

* cited by examiner

*Primary Examiner*—Elli Peselev
(74) *Attorney, Agent, or Firm*—Judy Jarecki-Black; Merial Limited; Thomas Kowalski, Esq.

(57) ABSTRACT

A compound of formula (I) wherein the bond between carbon atoms 22 and 23 may be a single or a double bond; $R_1$ is $C_1$-$C_{12}$alkyl, $C_3$-$C_8$cycloalkyl, or $C_2$-$C_{12}$alkenyl; $R_2$ and $R_3$ are, for example, independently of each other hydrogen, $C_1$-$C_{12}$alkyl, $C_3$-$C_{12}$cycloalkyl, $C_2$-$C_{12}$alkenyl, $C_2$-$C_{12}$alkynyl, aryl or heteroaryl; and, where applicable, to E/Z isomers, mixtures of E/Z isomers, diastereomers and/or tautomers, in each case in free form or in salt form; pesticidal compositions in which the active ingredient has been selected from those compounds and their tautomers; and a method of controlling pests using those compositions are described.

7 Claims, No Drawings

AVERMECTIN B1 MONOSACCHARIDE DERIVATIVES

This application is a 371 of International Application No. PCT/EP2004/006442 filed Jun. 15, 2004, which claims priority to GB0313937.5 filed Jun. 16, 2003, the contents of which are incorporated herein by reference.

The invention relates to (1) a compound of formula

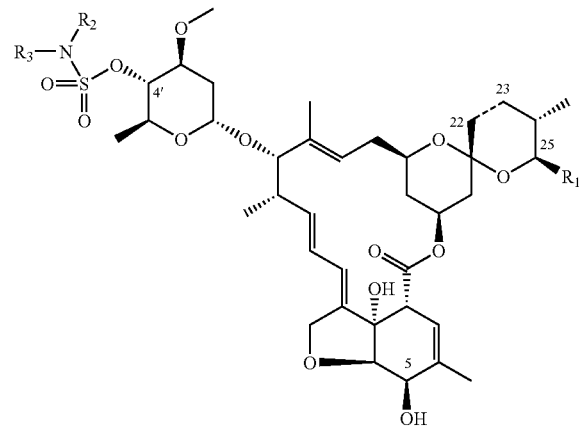

wherein the bond between carbon atoms 22 and 23 may be a single or a double bond;

$R_1$ is $C_1$-$C_{12}$alkyl, $C_3$-$C_8$cycloalkyl, or $C_2$-$C_{12}$alkenyl;

$R_2$ and $R_3$ are independently of each other hydrogen, $C_1$-$C_{12}$alkyl, $C_3$-$C_{12}$cycloalkyl, $C_2$-$C_{12}$alkenyl, $C_2$-$C_{12}$alkynyl, aryl or heteroaryl; wherein the $C_1$-$C_{12}$alkyl, $C_3$-$C_{12}$cycloalkyl, $C_2$-$C_{12}$alkenyl, $C_2$-$C_{12}$alkynyl, aryl and heteroaryl radicals may be unsubstituted or mono- to penta-substituted; —C(=O)$R_4$ or $SO_2R_4$; or $R_2$ and $R_3$ together are a three- to seven-membered alkylene bridge or a four- to seven-membered alkenylene bridge wherein one or two $CH_2$ groups in the alkylene or alkenylene may have been replaced by O, S or $NR_5$; or are a group =$N^+$=$N^-$;

and wherein the substituents of the alkyl, alkenyl, alkynyl, alkylene, alkenylene, cycloalkyl, aryl and heteroaryl radicals defined under $R_2$ and $R_3$ are selected from the group consisting of OH; =O; SH; =S; —$NH_2$; CN; $NO_2$; halogen; $C_1$-$C_{12}$alkyl; halo-$C_1$-$C_2$alkyl; $C_1$-$C_{12}$alkenyl; $C_2$-$C_6$alkynyl; $C_3$-$C_8$cycloalkyl which is unsubstituted or substituted by from one to three methyl groups; norbornenyl; $C_3$-$C_8$cycloalkenyl that is unsubstituted or substituted by from one to three methyl groups; $C_3$-$C_8$halocycloalkyl; $C_1$-$C_{12}$alkoxy; $C_1$-$C_6$-alkoxy-$C_1$-$C_6$alkyl; $C_1$-$C_6$alkoxy-$C_1$-$C_6$alkoxy; $C_1$-$C_6$alkoxy-$C_1$-$C_6$alkoxy-$C_1$-$C_6$alkyl; $C_2$-$C_{12}$alkenyloxy; $C_1$-$C_{12}$alkenyloxy-$C_1$-$C_6$alkoxy; $C_3$-$C_8$cycloalkoxy; $C_1$-$C_{12}$haloalkoxy; $C_1$-$C_{12}$alkylthio; $C_3$-$C_8$cycloalkylthio; $C_1$-$C_{12}$haloalkylthio; $C_1$-$C_{12}$alkylsulfinyl; $C_3$-$C_8$cycloalkylsulfinyl; $C_1$-$C_{12}$haloalkylsulfinyl; $C_3$-$C_8$halocycloalkylsulfinyl; $C_1$-$C_{12}$alkylsulfonyl; $C_3$-$C_8$cycloalkylsulfonyl; $C_1$-$C_{12}$haloalkylsulfonyl; $C_3$-$C_8$halocycloalkylsulfonyl; $C_2$-$C_8$alkenyl; $C_2$-$C_8$alkynyl; —NH($C_1$-$C_6$alkyl); —N($C_1$-$C_6$alkyl)$_2$; —C(=O)$R_6$; —NHC(=O)$R_7$; —P(=O)(O$C_1$-$C_6$alkyl)$_2$; aryl; heterocyclyl; aryloxy; and heterocyclyloxy;

wherein the aryl, heterocyclyl, aryloxy and heterocyclyloxy radicals are unsubstituted or, depending upon the possibilities of substitution at the ring, mono- to penta-substituted by substituents selected from the group consisting of OH; halogen; CN; $NO_2$; $C_1$-$C_{12}$alkyl; $C_3$-$C_8$cycloalkyl; $C_1$-$C_{12}$haloalkyl; $C_1$-$C_{12}$alkoxy; $C_1$-$C_{12}$haloalkoxy; $C_1$-$C_{12}$alkylthio; $C_1$-$C_{12}$haloalkylthio; $C_1$-$C_{12}$alkylsulfinyl; $C_1$-$C_{12}$alkylsulfonyl; $C_1$-$C_6$alkoxy-$C_1$-$C_6$alkyl; dimethylamino-$C_1$-$C_6$alkoxy; $C_2$-$C_8$alkenyl; $C_2$-$C_8$alkynyl; phenyl-$C_1$-$C_6$alkyl; phenoxy that is unsubstituted or substituted by from one to three substituents selected independently of one another from halogen, methoxy, trifluoromethyl and trifluoromethoxy; phenyl-$C_1$-$C_6$alkoxy that is unsubstituted or substituted in the aromatic ring by from one to three substituents selected independently of one another from halogen, methoxy, trifluoromethyl and trifluoromethoxy; phenyl-$C_2$-$C_6$alkenyl; phenyl-$C_2$-$C_6$alkynyl; methylenedioxy; —C(=O)$R_6$; —O—C(=O)$R_7$; —NH—C(=O)$R_7$; —$NH_2$; —NH($C_1$-$C_{12}$alkyl); —N($C_1$-$C_{12}$alkyl)$_2$; $C_1$-$C_6$alkylthio; $C_1$-$C_6$alkylsulfinyl; $C_3$-$C_8$cycloalkylsulfinyl; $C_1$-$C_6$haloalkylsulfinyl; $C_3$-$C_8$halocycloalkylsulfinyl; $C_1$-$C_6$alkylsulfonyl; $C_3$-$C_8$cycloalkylsulfonyl; $C_1$-$C_6$haloalkylsulfonyl; and $C_3$-$C_8$halocycloalkylsulfonyl;

$R_4$ is H; $C_1$-$C_8$alkyl; $C_1$-$C_8$alkyl that is mono- to hepta-substituted by substituents selected from the group consisting of halogen, nitro, $C_1$-$C_8$alkoxy, aryloxy, OH, SH, —$NH_2$, —NH($C_1$-$C_{12}$alkyl) and —N($C_1$-$C_{12}$alkyl)$_2$; $C_1$-$C_8$alkoxy; halo-$C_1$-$C_8$alkoxy; $C_3$-$C_8$cycloalkyl; $C_3$-$C_8$cycloalkoxy; $C_2$-$C_8$alkenyl; halo-$C_2$-$C_8$alkenyl; $C_2$-$C_8$alkenyloxy; halo-$C_2$-$C_8$alkenyloxy; $C_2$-$C_8$alkynyl; $C_2$-$C_8$alkynyloxy; —$NH_2$; —NH($C_1$-$C_{12}$alkyl); —N($C_1$-$C_{12}$alkyl)$_2$; aryl; aryloxy; benzyl; benzyloxy; heterocyclyl; heterocyclyloxy; heterocyclylmethyl; heterocyclylmethoxy; —NH-aryl; —NH-heterocyclyl; —N($C_1$-$C_6$alkyl)-aryl; or —N($C_1$-$C_6$alkyl)-heterocyclyl;

wherein the radicals aryl, aryloxy, benzyl, benzyloxy, heterocyclyl, heterocyclyloxy, heterocyclylmethyl, heterocyclylmethoxy, —NH-aryl, —NH-heterocyclyl, —N($C_1$-$C_6$alkyl)-aryl and —N($C_1$-$C_6$alkyl)-heterocyclyl are unsubstituted or, depending upon the possibilities of substitution at the ring, are in the ring substituted by from one to three substituents selected independently of one another from halogen, $C_1$-$C_{12}$alkyl, $C_1$-$C_{12}$haloalkyl, $C_1$-$C_{12}$alkoxy, $C_1$-$C_{12}$haloalkoxy, $C_1$-$C_6$alkoxy-$C_1$-$C_6$alkoxy, $C_1$-$C_{12}$alkylthio, $C_1$-$C_{12}$haloalkylthio, $C_1$-$C_{12}$alkylsulfinyl, $C_1$-$C_{12}$alkylsulfonyl, $C_2$-$C_8$alkenyloxy, $C_2$-$C_8$alkynyloxy, nitro, —$N_3$, and cyano;

$R_5$ is $C_1$-$C_8$alkyl, $C_3$-$C_8$cycloalkyl, $C_2$-$C_8$alkenyl, $C_2$-$C_8$alkynyl, benzyl, —C(=O)—$R_8$ or —C(=S)—$R_8$;

$R_6$ is H; OH; SH; $C_1$-$C_8$alkyl; $C_1$-$C_8$alkyl which is mono- to hepta-substituted by substituents selected from the group consisting of halogen, nitro, $C_1$-$C_8$alkoxy, aryloxy, OH, SH, —$NH_2$, —NH($C_1$-$C_{12}$alkyl) and —N($C_1$-$C_{12}$alkyl)$_2$; $C_1$-$C_8$alkoxy; halo-$C_1$-$C_8$alkoxy; $C_3$-$C_8$cycloalkyl; $C_3$-$C_8$cycloalkoxy; $C_2$-$C_8$alkenyl; $C_2$-$C_8$alkenyloxy; $C_2$-$C_8$alkynyl; $C_2$-$C_8$alkynyloxy; —$NH_2$; —NH($C_1$-$C_{12}$alkyl); —N($C_1$-$C_{12}$alkyl)$_2$; aryl; aryloxy; benzyl; benzyloxy; heterocyclyl; heterocyclyloxy; heterocyclylmethyl; or heterocyclylmethoxy;

wherein the radicals aryl, aryloxy, benzyl, benzyloxy, heterocyclyl, heterocyclyloxy, heterocyclylmethyl and heterocyclylmethoxy are unsubstituted or, depending upon the possibilities of substitution at the ring, are substituted by from one to three substituents selected independently of one another from halogen, $C_1$-$C_{12}$alkyl, $C_1$-$C_{12}$haloalkyl, $C_1$-$C_{12}$alkoxy, $C_1$-$C_{12}$haloalkoxy, $C_1$-$C_6$alkoxy-$C_1$-$C_6$alkoxy, $C_1$-$C_{12}$alkylthio, $C_1$-$C_{12}$haloalkylthio, $C_1$-$C_{12}$alkylsulfinyl, $C_1$-$C_{12}$alkylsulfonyl, $C_2$-$C_8$alkenyloxy, $C_2$-$C_8$alkynyloxy, nitro, —$N_3$, and cyano;

$R_7$ is H, $C_1$-$C_{12}$alkyl, $C_1$-$C_6$alkoxy-$C_1$-$C_6$alkyl, $C_1$-$C_{12}$haloalkyl, $C_2$-$C_8$alkenyl, $C_2$-$C_8$alkynyl, aryl, heterocyclyl, benzyl, —$NH_2$, —NH($C_1$-$C_{12}$alkyl), —N($C_1$-$C_{12}$alkyl)$_2$, —NH-phenyl or —N($C_1$-$C_{12}$alkyl)-phenyl;

$R_8$ is H, OH, SH, —$NH_2$, —NH($C_1$-$C_{12}$alkyl), —N($C_1$-$C_{12}$alkyl)$_2$, $C_1$-$C_{12}$alkyl, $C_1$-$C_{12}$haloalkyl, $C_1$-$C_{12}$alkoxy, $C_1$-$C_{12}$haloalkoxy, $C_1$-$C_6$alkoxy-$C_1$-$C_6$alkyl, $C_1$-$C_6$alkoxy-$C_1$-$C_6$alkoxy, $C_1$-$C_{12}$alkylthio, $C_1$-$C_{12}$alkylsulfinyl, $C_1$-$C_{12}$alkylsulfonyl, $C_2$-$C_8$alkenyloxy, $C_2$-$C_8$alkynyloxy, phenyl, phenoxy, benzyloxy, —NH-phenyl, —N($C_1$-$C_6$alkyl)-phenyl, —NH—$C_1$-$C_6$alkyl-C(=O)—$R_9$, —N($C_1$-$C_6$alkyl)-$C_1$-$C_6$alkyl-C(=O)—$R_9$, or phenyl, phenoxy, benzyloxy, —NH-phenyl or —N($C_1$-$C_6$alkyl)-phenyl, each of which is substituted in the aromatic ring by from one to three substituents selected independently of one another from halogen, $C_1$-$C_6$alkoxy, $C_1$-$C_6$haloalkyl and $C_1$-$C_6$haloalkoxy; and $R_9$ is H, OH, $C_1$-$C_{12}$alkyl, $C_1$-$C_{12}$alkoxy, $C_1$-$C_6$alkoxy-$C_1$-$C_6$alkoxy, $C_2$-$C_8$alkenyloxy, phenyl, phenoxy, benzyloxy, —$NH_2$, —NH($C_1$-$C_{12}$alkyl), —N($C_1$-$C_{12}$alkyl)$_2$, —NH-phenyl or —N($C_1$-$C_{12}$alkyl)-phenyl;

and, where applicable, to E/Z isomers, mixtures of E/Z isomers, diastereomers and/or tautomers, in each case in free form or in salt form;

to a process for the preparation of and to the use of those compounds and their isomers and tautomers; to starting materials for the preparation of the compounds of formula (I); to pesticidal compositions in which the active ingredient has been selected from the compounds of formula (I) and their tautomers; and to a method of controlling pests using those compositions.

Hereinbefore and hereinafter, the bond marked by the symbol ⌇ in formulae (I), (II) and (IV) indicates that the 4'-(S)-as well as the 4'-(R)-isomer is meant.

Certain macrolide compounds are proposed for pest control in the literature. The biological properties of those known compounds are not entirely satisfactory, however, for which reason there is a need to provide further compounds having pesticidal properties, especially for the control of insects and members of the order Acarina. That problem is solved according to the invention by the provision of the present compounds of formula (I).

The compounds claimed according to the invention are derivatives of avermectin. Avermectins are known to the person skilled in the art. They are a group of structurally closely related pesticidally active compounds which are obtained by fermentation of a strain of the microorganism *Streptomyces avermitilis*. Derivatives of avermectins can be obtained via conventional chemical syntheses.

The Avermectins which can be obtained from *Streptomyces avermitilis* are referred to as A1a, A1b, A2a, A2b, B1a, B1b, B2a and B2b. The compounds referred to as "A" and "B" have a methoxy radical and an OH group, respectively, in the 5-position. The "a" series and the "b" series are compounds in which the substituent $R_1$ (in position 25) is a sec-butyl radical and an isopropyl radical, respectively. The number 1 in the name of the compounds means that carbon atoms 22 and 23 are linked by double bonds; the number 2 means that they are linked by a single bond and that the C atom 23 carries an OH group. The above nomenclature is adhered to in the description of the present invention to denote the specific structure type in the not naturally occurring Avermectin derivatives according to the invention which corresponds to the naturally occurring Avermectin. The invention makes available especially the monosaccharide derivatives of compounds of the B1 series, in particular mixtures of the monosaccharide derivatives of Avermectin B1, especially B1a and B1b; along with derivatives having a single bond between carbon atoms 22 and 23; and derivatives having other substituents in the 25-position.

Some of the compounds of formula (I) may be in the form of tautomers. Accordingly, any reference to the compounds of formula (I) hereinbefore and hereinafter is to be understood, where applicable, as including also corresponding tautomers, even if the latter are not specifically mentioned in every case.

The compounds of formula (I) and, where applicable, their tautomers can form salts, for example, acid addition salts. These acid addition salts are formed, for example, with strong inorganic acids, such as mineral acids, for example, sulfuric acid, a phosphoric acid or a hydrohalic acid, with strong organic carboxylic acids, such as unsubstituted or substituted, for example, halo-substituted, $C_1$-$C_4$alkanecarboxylic acids, for example, acetic acid, unsaturated or saturated dicarboxylic acids, for example, oxalic acid, malonic acid, maleic acid, fumaric acid or phthalic acid, hydroxycarboxylic acids, for example, ascorbic acid, lactic acid, malic acid, tartaric acid or citric acid, or benzoic acid, or with organic sulfonic acids, such as unsubstituted or substituted, for example, halo-substituted, $C_1$-$C_4$alkane- or arylsulfonic acids, for example, methane- or p-toluene-sulfonic acid. Compounds of formula (I) that have at least one acidic group can furthermore form salts with bases. Suitable salts with bases are, for example, metal salts, such as alkali metal salts or alkaline earth metal salts, for example, sodium, potassium or magnesium salts, or salts with ammonia or with an organic amine, such as morpholine, piperidine, pyrrolidine, a mono-, di- or tri-lower alkylamine, for example, ethylamine, diethylamine, triethylamine or dimethylpropylamine, or a mono-, di- or trihydroxy-lower alkylamine, for example, mono-, di- or tri-ethanolamine. Corresponding internal salts may also be formed where appropriate. The free form is preferred. Among the salts of the compounds of formula (I), the agrochemically advantageous salts are preferred. Hereinbefore and hereinafter, any reference to the free compounds of formula (I) or their salts is to be understood as including, where appropriate, also the corresponding salts or the free compounds of formula (I), respectively. The same applies to tautomers of compounds of formula (I) and salts thereof.

Generally, a preparation of a compound of formula (I) results in a mixture of compounds, so the present invention also extends to a mixture containing compounds of formula (I), such as a mixture containing E and Z isomers, R and S diastereoisomers, compounds with $R_1$ is iPr and compounds with $R_1$ is sec-Bu or compounds of different tautomers, or a mixture thereof.

Unless defined otherwise, the general terms used hereinbefore and hereinafter have the meanings given below.

Unless defined otherwise, carbon-containing groups and compounds each contain from 1 up to and including 6, preferably from 1 up to and including 4, especially 1 or 2, carbon atoms.

Halogen—as a group per se and as a structural element of other groups and compounds, such as haloalkyl, haloalkoxy and haloalkylthio—is fluorine, chlorine, bromine or iodine, especially fluorine, chlorine or bromine, more especially fluorine or chlorine.

Alkyl—as a group per se and as a structural element of other groups and compounds, such as haloalkyl, alkoxy and alkylthio—is, in each case giving consideration to the number of carbon atoms contained in the group or compound in question, either straight-chained, i.e., methyl, ethyl, propyl, butyl, pentyl, hexyl, heptyl or octyl, or branched, e.g., isopropyl, isobutyl, sec-butyl, tert-butyl, isopentyl, neopentyl or isohexyl. Preferred number of carbon atoms in an alkyl group is between 1 to 6, such as 1 to 4.

Cycloalkyl—as a group per se and as a structural element of other groups and compounds, such as halocycloalkyl, cycloalkoxy and cycloalkylthio—is, in each case giving due consideration to the number of carbon atoms contained in the group or compound in question, cyclopropyl, cyclobutyl, cyclopentyl, cyclohexyl, cycloheptyl or cyclooctyl. Preferred number of carbon atoms in a cycloalkyl group is between 3 to 6, such as 3 to 4.

Alkenyl—as a group per se and as a structural element of other groups and compounds—is, giving due consideration to the number of carbon atoms and conjugated or isolated double bonds contained in the group in question, either straight-chained, e.g., vinyl, allyl, 2-butenyl, 3-pentenyl, 1-hexenyl, 1-heptenyl, 1,3-hexadienyl or 1,3-octadienyl, or branched, e.g., isopropenyl, isobutenyl, isoprenyl, tert-pentenyl, isohexenyl, isoheptenyl or isooctenyl. Alkenyl groups having from 3 to 12, especially from 3 to 6, more especially 3 or 4, carbon atoms are preferred. Preference is given to alkenyl groups having 3 to 12, in particular 3 to 6, especially 3 or 4, carbon atoms.

Alkynyl—as a group per se and as a structural element of other groups and compounds—is, in each case giving due consideration to the number of carbon atoms and conjugated or isolated double bonds contained in the group or compound in question, either straight-chained, e.g., ethynyl, propargyl, 2-butynyl, 3-pentynyl, 1-hexynyl, 1-heptynyl, 3-hexen-1-ynyl or 1,5-heptadien-3-ynyl, or branched, e.g., 3-methylbut-1-ynyl, 4-ethylpent-1-ynyl, 4-methylhex-2-ynyl or 2-methylhept-3-ynyl. Alkynyl groups having from 3 to 12, especially from 3 to 6, more especially 3 or 4, carbon atoms are preferred. Preference is given to alkynyl groups having 3 to 12, in particular 3 to 6, especially 3 or 4, carbon atoms.

Alkoxy—as a group per se and also as a structural element of other groups and compounds is, in each case taking into account the number of carbon atoms contained in each case in the group or compound in question, either straight-chain, e.g., methoxy, ethoxy or propoxy, or branched-chain, for example, isopropoxy, isobutyoxy, or sec-butoxy. One or more oxygen atoms can be present in the group. Preferred number of carbon atoms in an alkoxy group is between 1 to 6, such as 1 to 4. Similarly, the oxygen atom in the group alkenyloxy or alkynyloxy can be in any position and the preferred number of carbon atoms in either group is between 2 to 6, such as 2 to 4.

Alkylene and alkenylene are straight-chained or branched bridge members, especially —$CH_2$—$CH_2$—$CH_2$—, —$CH_2$—$CH_2$—$CH_2$—$CH_2$—, —$CH_2$—$CH_2$—$CH_2$—$CH_2$—$CH_2$—, —$CH_2(CH_3)CH_2$—$CH_2$—, —$CH_2C(CH_3)_2$—$CH_2$—, —$CH_2$—$CH$=$CH$—$CH_2$— or —$CH_2$—$CH$=$CH$—$CH_2$—$CH_2$—.

Halo-substituted carbon-containing groups and compounds, such as alkyl, alkenyl, alkynyl, cycloalkyl, alkoxy or alkylthio substituted by halogen, may be partially halogenated or perhalogenated, it being possible in the case of polyhalogenation for the halogen substituents to be the same or different. Examples of haloalkyl—as a group per se and as a structural element of other groups and compounds, such as haloalkoxy and haloalkylthio—are methyl substituted from one to three times by fluorine, chlorine and/or bromine, such as $CHF_2$ or $CF_3$; ethyl substituted from one to five times by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl substituted from one to seven times by fluorine, chlorine and/or bromine, such as $CH_2CHBrCH_2Br$, $CF_2CHFCF_3$, $CH_2CF_2CF_3$, $CH(CF_3)_2$ or $CF(CF_3)_2$; butyl or an isomer thereof substituted from one to nine times by fluorine, chorine and/or bromine, such as $CF(CF_3)CHFCF_3$ or $CH_2(CF_2)_2CF_3$; pentyl or an isomer thereof substituted from one to eleven times by fluorine, chlorine and/or bromine, such as $CF(CF_3)(CHF)_2CF_3$ or $CH_2(CF_2)_3CF_3$; and hexyl or an isomer thereof substituted from one to thirteen times by fluorine, chlorine and/or bromine, such as $(CH_2)_4CHBrCH_2Br$, $CF_2(CHF)_4CF_3$, $CH_2(CF_2)_4CF_3$ or $C(CF_3)_2(CHF)_2CF_3$.

Aryl is especially phenyl, naphthyl, anthracenyl or perylenyl, preferably phenyl.

Heterocyclyl is understood as being a three- to seven-membered monocyclic ring, which may be saturated or unsaturated, and that contains from one to three hetero atoms selected from the group consisting of N, O and S, especially N and S; or a bicyclic ring-system having from 8 to 14 ring atoms, which may be saturated or unsaturated, and that may contain either in only one ring or in both rings independently of one another, one or two hetero atoms selected from N, O and S. Heterocyclyl is especially pyridyl, pyrimidyl, s-triazinyl, 1,2,4-triazinyl, thienyl, furyl, tetrahydrofuranyl, pyranyl, tetrahydropyranyl, pyrrolyl, pyrazolyl, imidazolyl, thiazolyl, triazolyl, tetrazolyl, oxazolyl, thiadiazolyl, oxadiazolyl, benzothienyl, quinolinyl, quinoxalinyl, benzofuranyl, benzimidazolyl, benzopyrrolyl, benzothiazolyl, indolyl, coumarinyl or indazolyl, which are preferably bonded via a carbon atom; preference is given to thienyl, thiazolyl, benzofuranyl, benzothiazolyl, furyl, tetrahydropyranyl and indolyl; especially pyridyl or thiazolyl.

Within the scope of the present invention, preference is given to (2) compounds according to group (1) of formula (I) wherein $R_2$ is H; $C_1$-$C_8$alkyl; $C_1$-$C_8$-alkyl mono- to penta-substituted by substituents selected from the group consisting of halogen, OH, $C_1$-$C_4$alkoxy and CN; $C_3$-$C_{12}$alkenyl, $C_3$-$C_{12}$alkynyl; or C(=O)$R_4$;

(3) compounds according to group (2) of formula (I) wherein $R_2$ is $C_1$-$C_4$alkyl, especially methyl;

(4) compounds according to group (2) of formula (I) wherein $R_2$ is ethyl;

(5) compounds according to group (2) of formula (I) wherein $R_2$ is n-propyl;

(6) compounds according to any one of groups (1) to (5) of formula (I) wherein $R_3$ is H, $C_1$-$C_8$alkyl, $C_3$-$C_{12}$alkenyl, $C_3$-$C_{12}$alkynyl, or $C_1$-$C_8$alkyl substituted by substituents selected from the group consisting of halogen, OH and CN;

(7) compounds according to group (6) of formula (I) wherein $R_3$ is H;

(8) compounds according to group (6) of formula (I) wherein $R_3$ is methyl;

(9) compounds according to group (6) of formula (I) wherein $R_3$ is ethyl;

(10) compounds according to group (6) of formula (I) wherein $R_3$ is n-propyl;

(11) compounds according to group (6) of formula (I) wherein $R_3$ is isopropyl;

(12) compounds according to any one of groups (2) and (6) to (11) of formula (I) wherein $R_2$ is —C(=O)$R_4$ and $R_4$ is H, $C_1$-$C_4$alkyl, $C_1$-$C_4$alkoxy, halo-$C_1$-$C_4$alkyl, halo-$C_1$-$C_4$alkoxy, $C_3$-$C_8$cycloalkoxy, $C_2$-$C_8$alkenyloxy, $C_2$-$C_8$alkynyloxy, —$NH_2$, —NH($C_1$-$C_{12}$alkyl), —N($C_1$-$C_{12}$alkyl)$_2$, aryl, aryloxy, benzyl, or benzyloxy; wherein the radicals aryl, aryloxy, benzyl and benzyloxy are unsubstituted or substituted by from one to three substituents selected independently of one another from halogen, $C_1$-$C_4$alkyl, $C_1$-$C_4$haloalkyl, $C_1$-$C_4$alkoxy, $C_1$-$C_4$haloalkoxy, $C_1$-$C_{12}$haloalkylthio, nitro and cyano;

(13) compounds according to group (1) of formula (I) wherein $R_2$ and $R_3$ together are —$CH_2$—$CH_2$—$CH_2$— or —$CH_2$—$CH_2$—$CH_2$—$CH_2$—;

(14) compounds according to group (1) of formula (I) wherein $R_2$ and $R_3$ together are —$CH_2$—$CH_2$—O—$CH_2$—$CH_2$— or —$CH_2$—$CH_2$—N($CH_3$)—$CH_2$—$CH_2$—;

(15) compounds according to any one of groups (1) and (6) to (11) of formula (I) wherein $R_2$ is substituted $C_1$-$C_4$alkyl, especially —$CH_2$—, and the substituents are selected from the group consisting of OH, CN, halogen, $C_3$-$C_8$cycloalkyl, $C_3$-$C_8$cycloalkenyl that is unsubstituted or substituted by from one to three methyl groups, $C_1$-$C_{12}$alkoxy, $C_2$-$C_8$alkynyl, —C(=O)$R_6$, —NHC(=O)$R_7$, —P(=O)(O$C_1$-$C_6$alkyl)$_2$, and unsubstituted or, depending upon the possibilities of substitution at the ring, mono- to penta-substituted phenyl, naphthyl, anthracenyl, phenanthrenyl, fluorenyl, perylenyl and heterocyclyl;

especially preferred are substituents on the $C_1$-$C_4$alkyl which are selected from the group consisting of halogen, CN, $C_3$-$C_8$cycloalkyl, $C_2$-$C_8$alkynyl, —C(=O)$R_6$, —NHC(=O)$R_7$, —P(=O)(O$C_1$-$C_6$alkyl)$_2$, and unsubstituted or, depending upon the possibilities of substitution at the ring, mono- to tri-substituted phenyl, naphthyl, anthracenyl, pyridyl, thiazolyl, imidazolyl, furyl, quinolinyl and pyrazolyl;

(16) compounds according to any one of groups (1), (6) to (11) of formula (I) wherein $R_2$ is benzyl that is unsubstituted or carries on the aromatic moiety from one to three substituents that are selected from the group consisting of halogen, CN, NO$_2$, $C_1$-$C_{12}$alkyl, $C_3$-$C_8$cycloalkyl, $C_1$-$C_{12}$haloalkyl, $C_1$-$C_{12}$alkoxy, $C_1$-$C_{12}$haloalkoxy, $C_1$-$C_{12}$alkylthio, $C_1$-$C_{12}$haloalkylthio, $C_1$-$C_{12}$alkylsulfinyl, $C_1$-$C_{12}$alkylsulfonyl, $C_1$-$C_6$alkoxy-$C_1$-$C_6$alkyl, $C_2$-$C_8$alkenyl, $C_2$-$C_8$-alkynyl, phenoxy, phenyl-$C_1$-$C_6$alkyl, methylenedioxy, —C(=O)$R_6$, —O—C(=O)$R_7$, —NH—C(=O)$R_7$, —NH$_2$, —NH($C_1$-$C_{12}$alkyl), —N($C_1$-$C_{12}$alkyl)$_2$, $C_1$-$C_6$alkylthio, $C_1$-$C_6$alkylsulfinyl, $C_3$-$C_8$cycloalkylsulfinyl, $C_1$-$C_6$haloalkylsulfinyl, $C_3$-$C_8$halocycloalkylsulfinyl, $C_1$-$C_6$alkylsulfonyl, $C_3$-$C_8$cycloalkylsulfonyl, $C_1$-$C_6$haloalkylsulfonyl ard $C_3$-$C_8$halocycloalkylsulfonyl;

wherein $R_6$ is H, OH, SH, $C_1$-$C_8$alkyl, $C_1$-$C_8$alkyl that is mono- to hepta-substituted by substituents selected from halogen, nitro, $C_1$-$C_8$alkoxy, aryloxy, OH, SH, —NH$_2$, —NH($C_1$-$C_{12}$alkyl) and —N($C_1$-$C_{12}$alkyl)$_2$, $C_1$-$C_8$alkoxy, halo-$C_1$-$C_8$alkoxy, $C_3$-$C_8$cycloalkyl, $C_3$-$C_8$cycloalkoxy, —NH$_2$, —NH($C_1$-$C_{12}$alkyl), —N($C_1$-$C_{12}$alkyl)$_2$, aryl, aryloxy, benzyl, benzyloxy, heterocyclyl, heterocyclyloxy, heterocyclylmethyl or heterocyclylmethoxy; and $R_7$ is H, $C_1$-$C_{12}$alkyl, $C_1$-$C_6$alkoxy-$C_1$-$C_6$alkyl, $C_1$-$C_{12}$haloalkyl, aryl, heterocyclyl, benzyl, —NH$_2$, —NH($C_1$-$C_{12}$alkyl), —N($C_1$-$C_{12}$alkyl)$_2$, —NH-phenyl or —N($C_1$-$C_{12}$alkyl)-phenyl;

(17) compounds according to any one of groups (1) and (6) to (11) of formula (I) wherein $R_2$ is $C_1$-$C_4$alkyl-C(=O)$R_6$, especially —CH$_2$—C(=O)$R_6$; and wherein $R_6$ is H, OH, —NH$_2$, —NH($C_1$-$C_2$alkyl), —N($C_1$-$C_2$alkyl)$_2$, $C_1$-$C_4$alkyl, $C_1$-$C_{12}$alkoxy, $C_2$-$C_4$alkenyloxy, —NH—$C_1$-$C_2$alkyl-C(=O)—O—$C_1$-$C_2$alkyl-phenyl, —P(=O)(O$C_1$-$C_6$alkyl)$_2$, or phenyl, phenoxy, benzyloxy or NH-phenyl that is unsubstituted or substituted by substituents selected from chlorine, fluorine, methoxy, trifluoromethyl and trifluoromethoxy;

more especially $R_6$ is $C_1$-$C_{12}$alkoxy;

(18) compounds according to any one of groups (1) to (17) of formula (I) that have the (R)-configuration at the 4'-position;

(19) compounds according to any one of groups (1) to (17) of formula (I) that have the (S)-configuration at the 4'-position;

(20) compounds according to any one of groups (1) to (19) of formula (I) wherein $R_1$ is isopropyl or sec-butyl, preferably wherein a mixture of the isopropyl and the sec-butyl derivative is present;

(21) compounds according to any one of groups (1) to (19) of formula (I) wherein $R_1$ is cyclohexyl;

(22) compounds according to any one of groups (1) to (19) of formula (I) wherein $R_1$ is 1-methyl-butyl;

(23) compounds according to any one of groups (1) to (22) of formula (I) wherein the bond between carbon atoms 22 and 23 is a single bond;

(24) compounds according to any one of groups (1) to (22) of formula (I) wherein the bond between carbon atoms 22 and 23 is a double bond.

Special preference is given within the scope of the invention to compounds P.1 to P.4, to compounds A.1 to A.20 and to the compounds listed in the Tables 1 to 36 and, where applicable, their E/Z isomers and mixtures of E/Z isomers.

In the context of the invention, a particular reference is made to compounds of formula (Ia) or (Ib) as indicated in Tables 1 to 36.

TABLE B

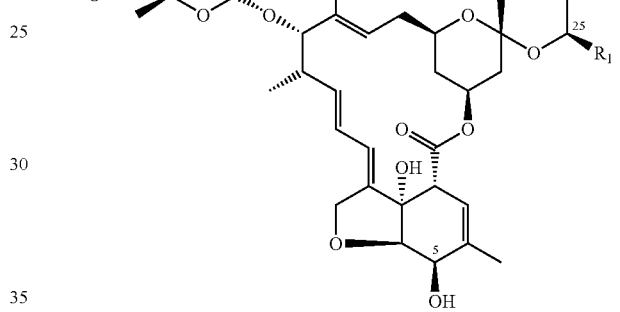

(Ia)

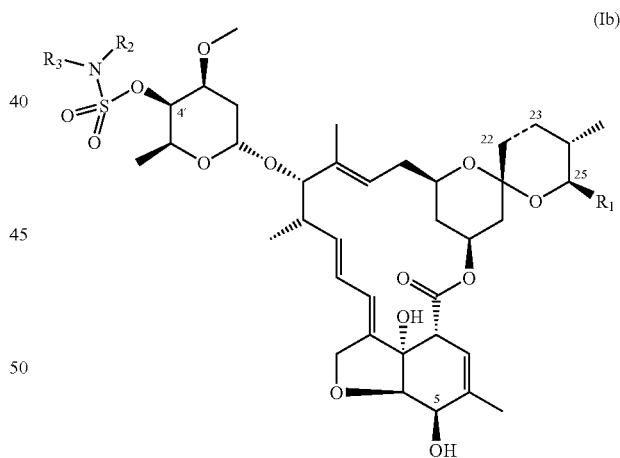

(Ib)

Compounds of formula (Ia) or (Ib), where

| No. | $R_2$ |
|---|---|
| B.1 | isopropyl |
| B.2 | propyl |
| B.3 | n-butyl |
| B.4 | sec-butyl |
| B.5 | isobutyl |
| B.6 | tert-butyl |
| B.7 | CH(CH$_3$)CH(CH$_3$)$_2$ |
| B.8 | CH(CH$_2$CH$_3$)CH$_2$Cl |
| B.9 | CH(CH$_3$)CH$_2$OCH$_3$ |
| B.10 | 2-chloro-propyl |
| B.11 | 3-chloro-propyl |
| B.12 | 2-chloro-ethyl |

TABLE B-continued

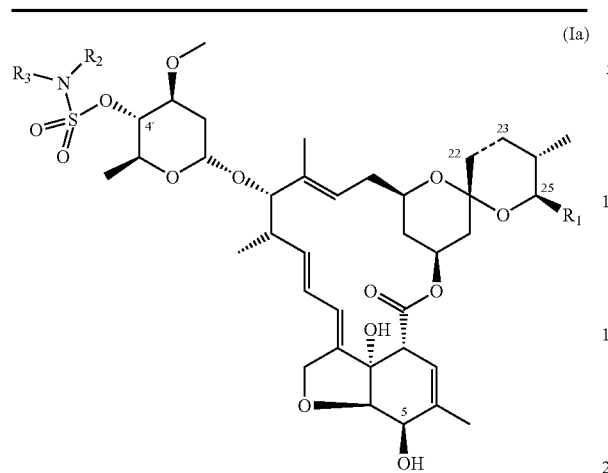

(Ia)

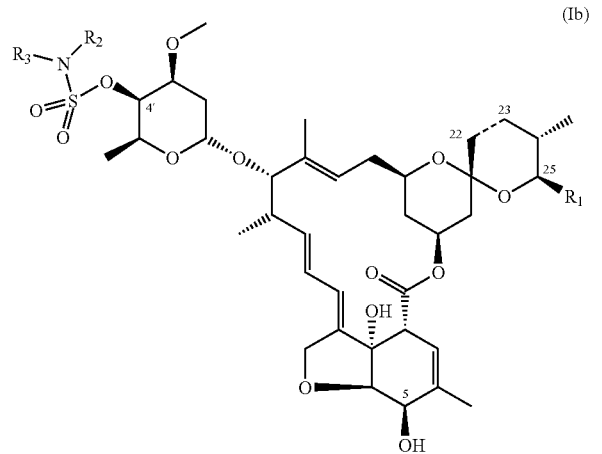

(Ib)

Compounds of formula (Ia) or (Ib), where

| No. | $R_2$ |
|---|---|
| B.13 | $CH_2CH_2OCH_3$ |
| B.14 | 2-fluoro-ethyl |
| B.15 | 2-(morpholine-4-yl)ethyl |
| B.16 | 2-(pyrrolidine-1-yl)ethyl |
| B.17 | cyclopropyl |
| B.18 | cyclobutyl |
| B.19 | cyclopentyl |
| B.20 | cyclohexyl |
| B.21 | bis(trifluoromethyl)methyl |
| B.22 | benzyl |
| B.23 | 2-methylallyl |
| B.24 | 3-methylallyl |
| B.25 | $CH_2C(O)OCH_3$ |
| B.26 | $CH_2CH_2C(O)OCH_3$ |
| B.27 | 2-(1,3-dioxo-1,3-dihydro-isoindol-2-yl)ethyl |
| B.28 | 2-aminoethyl |
| B.29 | 2-methylaminoethyl |
| B.30 | 2-dimethylaminoethyl |
| B.31 | $CH_2CH_2OC_2H_5$ |
| B.32 | $CH_2CH_2OCH_2CH_2OCH_3$ |
| B.33 | 3-(1,3-dioxo-1,3-dihydro-isoindol-2-yl)propyl |
| B.34 | 4-(1,3-dioxo-1,3-dihydro-isoindol-2-yl)-butyl |
| B.35 | $CH_2CONH_2$ |
| B.36 | $CH_2COOH$ |
| B.37 | (2-fluorophenyl)methyl |
| B.38 | (3-fluorophenyl)methyl |
| B.39 | (2,6-difluorophenyl)methyl |
| B.40 | (4-fluorophenyl)methyl |
| B.41 | (4-trifluoromethylphenyl)methyl |

TABLE B-continued

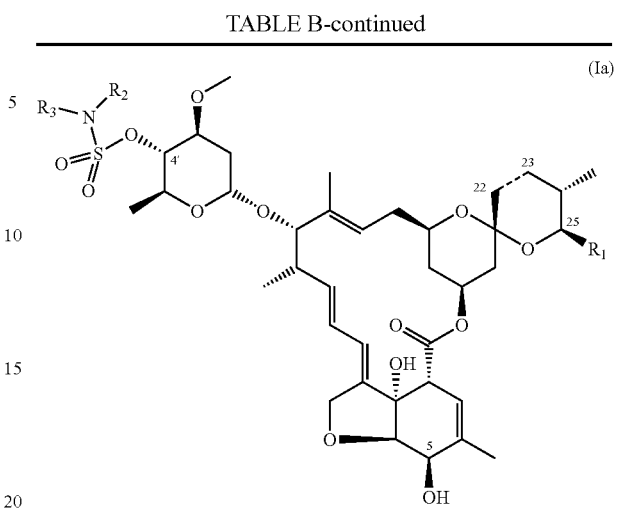

(Ia)

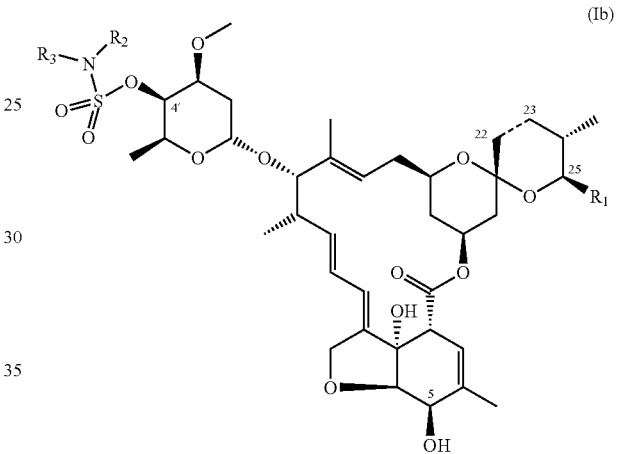

(Ib)

Compounds of formula (Ia) or (Ib), where

| No. | $R_2$ |
|---|---|
| B.42 | 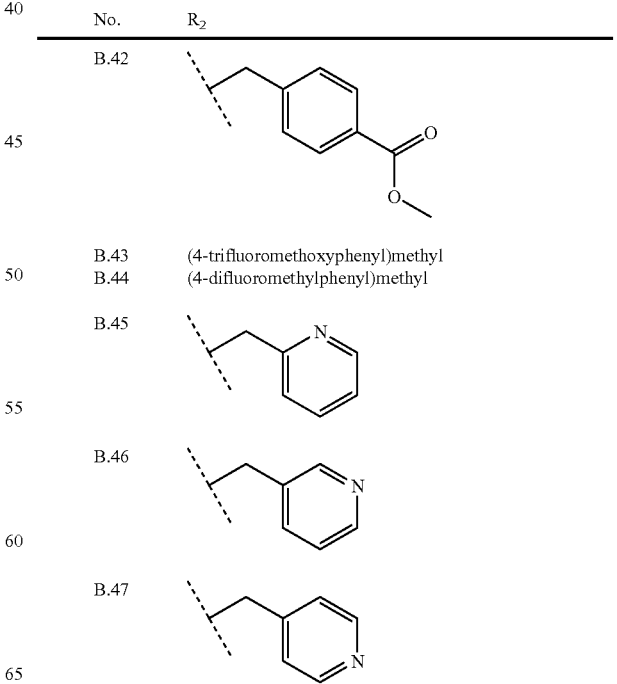 |
| B.43 | (4-trifluoromethoxyphenyl)methyl |
| B.44 | (4-difluoromethylphenyl)methyl |
| B.45 | |
| B.46 | |
| B.47 | |

TABLE B-continued

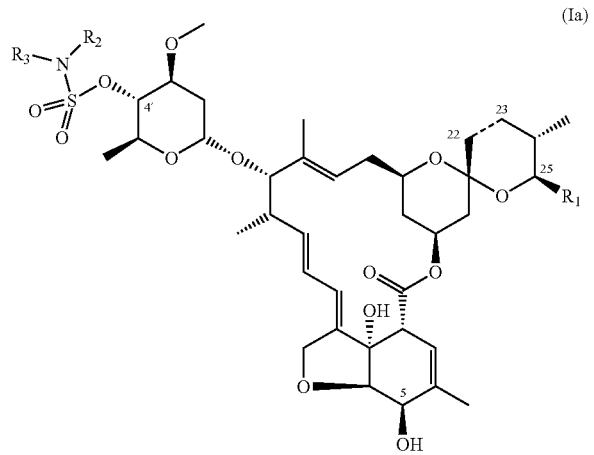

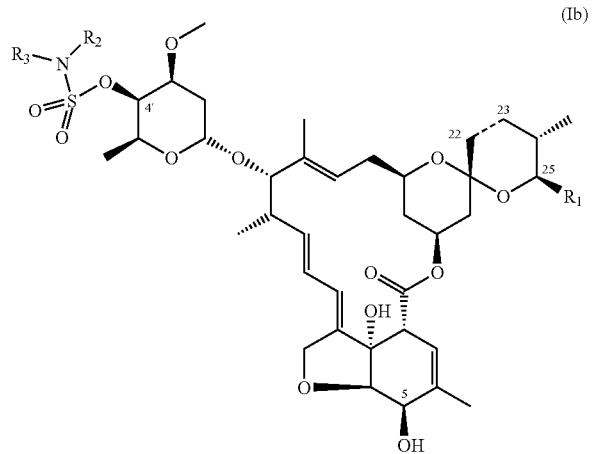

Compounds of formula (Ia) or (Ib), where

| No. | R$_2$ |
|---|---|
| B.48 | (5-methyl-isoxazol-3-yl)methyl structure |
| B.49 | (4-cyanophenyl)methyl structure |
| B.50 | (4-methoxyphenyl)methyl |
| B.51 | phenyl |
| B.52 | 4-chlorophenyl |
| B.53 | Pyrid-3-yl |
| B.54 | 2-chloropyrid-5-yl |

Table 1: A compound of formula (Ia) wherein R$_1$ is sec-butyl (B1a) or isopropyl (B1b), R$_3$ is hydrogen, the bond between carbon atoms 22 and 23 is a double bond and R$_2$ corresponds to one of the radicals of Table B listed under B.1 to B.54.

Table 2: A compound of formula (Ia) wherein R$_1$ is sec-butyl (B1a) or isopropyl (B1b), R$_3$ is hydrogen, the bond between carbon atoms 22 and 23 is a single bond and R$_2$ corresponds to one of the radicals of Table B listed under B.1 to B.54.

Table 3: A compound of formula (Ib) wherein R$_1$ is sec-butyl (B1a) or isopropyl (B1b), R$_3$ is hydrogen, the bond between carbon atoms 22 and 23 is a double bond and R$_2$ corresponds to one of the radicals of Table B listed under B.1 to B.54.

Table 4: A compound of formula (Ib) wherein R$_1$ is sec-butyl (B1a) or isopropyl (B1b), R$_3$ is hydrogen, the bond between carbon atoms 22 and 23 is a single bond and R$_2$ corresponds to one of the radicals of Table B listed under B.1 to B.54.

Table 5: A compound of formula (Ia) wherein R$_1$ is cyclohexyl, R$_3$ is hydrogen, the bond between carbon atoms 22 and 23 is a double bond and R$_2$ corresponds to one of the radicals of Table B listed under B.1 to B.54.

Table 6: A compound of formula (Ia) wherein R$_1$ is cyclohexyl, R$_3$ is hydrogen, the bond between carbon atoms 22 and 23 is a single bond and R$_2$ corresponds to one of the radicals of Table B listed under B.1 to B.54.

Table 7: A compound of formula (Ib) wherein R$_1$ is cyclohexyl, R$_3$ is hydrogen, the bond between carbon atoms 22 and 23 is a double bond and R$_2$ corresponds to one of the radicals of Table B listed under B.1 to B.54.

Table 8: A compound of formula (Ib) wherein R$_1$ is cyclohexyl, R$_3$ is hydrogen, the bond between carbon atoms 22 and 23 is a single bond and R$_2$ corresponds to one of the radicals of Table B listed under B.1 to B.54.

Table 9: A compound of formula (Ia) wherein R$_1$ is 1-methyl-butyl, R$_3$ is hydrogen, the bond between carbon atoms 22 and 23 is a double bond and R$_2$ corresponds to one of the radicals of Table B listed under B.1 to B.54.

Table 10: A compound of formula (Ia) wherein R$_1$ is 1-methyl-butyl, R$_3$ is hydrogen, the bond between carbon atoms 22 and 23 is a single bond and R$_2$ corresponds to one of the radicals of Table B listed under B.1 to B.54.

Table 11: A compound of formula (Ib) wherein R$_1$ is 1-methyl-butyl, R$_3$ is hydrogen, the bond between carbon atoms 22 and 23 is a double bond and R$_2$ corresponds to one of the radicals of Table B listed under B.1 to B.54.

Table 12: A compound of formula (Ib) wherein R$_1$ is 1-methyl-butyl, R$_3$ is hydrogen, the bond between carbon atoms 22 and 23 is a single bond and R$_2$ corresponds to one of the radicals of Table B listed under B.1 to B.54.

TABLE C

Compounds of formula (Ia) or (Ib), where

| No. | R$_4$ |
|---|---|
| C.1 | Isopropyl |
| C.2 | Propyl |
| C.3 | n-butyl |
| C.4 | sec-butyl |
| C.5 | Isobutyl |
| C.6 | tert-butyl |
| C.7 | methyl |
| C.8 | ethyl |
| C.9 | vinyl |
| C.10 | 2-chloro-propyl |
| C.11 | 3-chloro-propyl |
| C.12 | 2-chloro-ethyl |
| C.13 | $CH_2CH_2OCH_3$ |
| C.14 | allyl |
| C.15 | $CH_2OCH_3$ |
| C.16 | $CH_2O$phenyl |
| C.17 | cyclopropyl |
| C.18 | cyclopentyl |

TABLE C-continued

Compounds of formula (Ia) or (Ib), where

| No. | $R_4$ |
|---|---|
| C.19 | cyclohexyl |
| C.20 | $CH_2CH_2NH_2$ |
| C.21 | benzyl |
| C.22 | fluoromethyl |
| C.23 | difluoromethyl |
| C.24 | (thiophene-methyl structure) |
| C.25 | (tetrazole-methyl structure) |
| C.26 | $CH_2OCH_2CH_2OCH_3$ |
| C.27 | $OCH_3$ |
| C.28 | $OCH_2CH_3$ |
| C.29 | O-allyl |
| C.30 | $OCH_2CH_2OH$ |
| C.31 | $NH_2$ |
| C.32 | $NHCH_3$ |
| C.33 | $N(CH_3)$ |
| C.34 | Benzyl |
| C.35 | phenyl |
| C.36 | 4-chlorophenyl |
| C.37 | pyrid-3-yl |
| C.38 | 2-chloropyrid-5-yl |

Table 13: A compound of formula (Ia) wherein $R_1$ is sec-butyl (B1a) or isopropyl (B1b), the bond between carbon atoms 22 and 23 is a double bond, $R_2$ is $C(=O)R_4$ and $R_3$ is hydrogen, and $R_4$ corresponds to one of the radicals of Table C listed under C.1 to C.38.

Table 14: A compound of formula (Ib) wherein $R_1$ is sec-butyl (B1a) or isopropyl (B1b), the bond between carbon atoms 22 and 23 is a double bond, $R_2$ is $—C(=O)R_4$ and $R_3$ is hydrogen, and $R_4$ corresponds to one of the radicals of Table C listed under C.1 to C.38.

Table 15: A compound of formula (Ia) wherein $R_1$ is sec-butyl (B1a) or isopropyl (B1b), the bond between carbon atoms 22 and 23 is a single bond, $R_2$ is $C(=O)R_4$ and $R_3$ is hydrogen, and $R_4$ corresponds to one of the radicals of Table C listed under C.1 to C.38.

Table 16: A compound of formula (Ib) wherein $R_1$ is sec-butyl (B1a) or isopropyl (B1b), the bond between carbon atoms 22 and 23 is a single bond, $R_2$ is $—C(=O)R_4$ and $R_3$ is hydrogen, and $R_4$ corresponds to one of the radicals of Table C listed under C.1 to C.38.

Table 17: A compound of formula (Ia) wherein $R_1$ is cyclohexyl, the bond between carbon atoms 22 and 23 is a double bond, $R_2$ is $C(=O)R_4$ and $R_3$ is hydrogen, and $R_4$ corresponds to one of the radicals of Table C listed under C.1 to C.38.

Table 18: A compound of formula (Ib) wherein $R_1$ is cyclohexyl, the bond between carbon atoms 22 and 23 is a double bond, $R_2$ is $—C(=O)R_4$ and $R_3$ is hydrogen, and $R_4$ corresponds to one of the radicals of Table C listed under C.1 to C.38.

Table 19: A compound of formula (Ia) wherein $R_1$ is cyclohexyl, the bond between carbon atoms 22 and 23 is a single bond, $R_2$ is $C(=O)R_4$ and $R_3$ is hydrogen, and $R_4$ corresponds to one of the radicals of Table C listed under C.1 to C.38.

Table 20: A compound of formula (Ib) wherein $R_1$ is cyclohexyl, the bond between carbon atoms 22 and 23 is a single bond, $R_2$ is $—C(=O)R_4$ and $R_3$ is hydrogen, and $R_4$ corresponds to one of the radicals of Table C listed under C.1 to C.38.

Table 21: A compound of formula (Ia) wherein $R_1$ is 1-methyl-butyl, the bond between carbon atoms 22 and 23 is a double bond, $R_2$ is $C(=O)R_4$ and $R_3$ is hydrogen, and $R_4$ corresponds to one of the radicals of Table C listed under C.1 to C.38.

Table 22: A compound of formula (Ib) wherein $R_1$ is 1-methyl-butyl, the bond between carbon atoms 22 and 23 is a double bond, $R_2$ is $—C(=O)R_4$ and $R_3$ is hydrogen, and $R_4$ corresponds to one of the radicals of Table C listed under C.1 to C.38.

Table 23: A compound of formula (Ia) wherein $R_1$ is 1-methyl-butyl, the bond between carbon atoms 22 and 23 is a single bond, $R_2$ is $C(=O)R_4$ and $R_3$ is hydrogen, and $R_4$ corresponds to one of the radicals of Table C listed under C.1 to C.38.

Table 24: A compound of formula (Ib) wherein $R_1$ is 1-methyl-butyl, the bond between carbon atoms 22 and 23 is a single bond, $R_2$ is $—C(=O)R_4$ and $R_3$ is hydrogen, and $R_4$ corresponds to one of the radicals of Table C listed under C.1 to C.38.

TABLE D

Compounds of formula (Ia) or (Ib), where

| No. | $R_2$ | $R_3$ |
|---|---|---|
| D.1 | | $—CH_2CH_2—$ |
| D.2 | | $—CH_2CH_2CH_2—$ |
| D.3 | | $—CH_2(CH_2)_3CH_2—$ |
| D.4 | | $—CH_2CH_2OCH_2CH_2—$ |
| D.5 | ethyl | ethyl |
| D.6 | ethyl | methyl |
| D.7 | allyl | methyl |
| D.8 | $CH_2CH_2OH$ | methyl |
| D.9 | $C(O)CH_3$ | methyl |
| D.10 | $C(O)OCH_3$ | methyl |
| D.11 | $C(O)Ph$ | methyl |
| D.12 | $SO_2NH_2$ | H |
| D.13 | $SO_2NMe_2$ | H |
| D.14 | | $=N^+=N^-$ |
| D.15 | benzyl | benzyl |
| D.16 | (4-trifluoromethoxybenzyl) | (4-trifluoromethoxybenzyl) |
| D.17 | (4-methoxyphenyl)methyl | (4-methoxyphenyl)methyl |
| D.18 | | $—CH_2CH_2N(CH_3)CH_2CH_2—$ |
| D.19 | | $—CH_2CH_2N(CH_2CH=CH_2)CH_2CH_2—$ |
| D.20 | | $—CH_2CH_2N[C(=O)CH_3]CH_2CH_2—$ |
| D.21 | propargyl | H |
| D.22 | | $—CH_2CH_2CH_2—$ |
| D.23 | $—CH_2OCH_2CH_2OCH_3$ | H |
| D.24 | $C(O)CH_2OC_6H_5$ | H |
| D.25 | allyl | H |
| D.26 | $—C(=O)C_2H_5$ | H |
| D.27 | $—CH_2OCH_2CH_2OCH_3$ | $—CH_2OCH_2CH_2OCH_3$ |
| D.28 | methyl | H |
| D.29 | methyl | methyl |
| D.30 | ethyl | H |
| D.31 | propargyl | methyl |
| D.32 | phenyl | H |
| D.33 | phenyl | methyl |
| D.34 | $CH_3—O—CH_2—$ | H |

TABLE D-continued

Compounds of formula (Ia) or (Ib), where

| No. | $R_2$ | $R_3$ |
|---|---|---|
| D.35 | $CH_3-O-CH_2-$ | methyl |
| D.36 | $CH_3-O-CH_2-$ | $CH_3-O-CH_2-$ |
| D.37 | $-CH_2-CN$ | H |
| D.38 | $-CH_2-CN$ | $-CH_2-CN$ |
| D.39 | $CH_3-O-C(=O)-$ | H |
| D.40 | $H-C(=O)-$ | H |
| D.41 | $CH_3-SO_2-$ | H |
| D.42 | $NH_2-SO_2-$ | H |
| D.43 | $NH_2-C(=O)-$ | H |
| D.44 | $CF_3-C(=O)-$ | H |
| D.45 | $HO-CH_2-CH_2-$ | H |
| D.46 | $HO-CH_2-CH_2-$ | $HO-CH_2-CH_2-$ |

Table 25: A compound of formula (Ia) wherein $R_1$ is sec-butyl (B1a) or isopropyl (B1b), the bond between carbon atoms 22 and 23 is a single bond, and the combination of $R_2$ and $R_3$ for each compound corresponds to a line D.1 to D.46 of Table D.

Table 26: A compound of formula (Ia) wherein $R_1$ is sec-butyl (B1a) or isopropyl (B1b), the bond between carbon atoms 22 and 23 is a double bond, and the combination of $R_2$ and $R_3$ for each compound corresponds to a line D.1 to D.46 of Table D.

Table 27: A compound of formula (Ib) wherein $R_1$ is sec-butyl (B1a) or isopropyl (B1b), the bond between carbon atoms 22 and 23 is a single bond, and the combination of $R_2$ and $R_3$ for each compound corresponds to a line D.1 to D.46 of Table D.

Table 28: A compound of formula (Ib) wherein $R_1$ is sec-butyl (B1a) or isopropyl (B1b), the bond between carbon atoms 22 and 23 is a double bond, and the combination of $R_2$ and $R_3$ for each compound corresponds to a line D.1 to D.46 of Table D.

Table 29: A compound of formula (Ia) wherein $R_1$ is cyclohexyl, the bond between carbon atoms 22 and 23 is a single bond, and the combination of $R_2$ and $R_3$ for each compound corresponds to a line D.1 to D.46 of Table D.

Table 30: A compound of formula (Ia) wherein $R_1$ is cyclohexyl, the bond between carbon atoms 22 and 23 is a double bond, and the combination of $R_2$ and $R_3$ for each compound corresponds to a line D.1 to D.46 of Table D.

Table 31: A compound of formula (Ib) wherein $R_1$ is cyclohexyl, the bond between carbon atoms 22 and 23 is a single bond, and the combination of $R_2$ and $R_3$ for each compound corresponds to a line D.1 to D.46 of Table D.

Table 32: A compound of formula (Ib) wherein $R_1$ is cyclohexyl, the bond between carbon atoms 22 and 23 is a double bond, and the combination of $R_2$ and $R_3$ for each compound corresponds to a line D.1 to D.46 of Table D.

Table 33: A compound of formula (Ia) wherein $R_1$ is 1-methyl-butyl, the bond between carbon atoms 22 and 23 is a single bond, and the combination of $R_2$ and $R_3$ for each compound corresponds to a line D.1 to D.46 of Table D.

Table 34: A compound of formula (Ia) wherein $R_1$ is 1-methyl-butyl, the bond between carbon atoms 22 and 23 is a double bond, and the combination of $R_2$ and $R_3$ for each compound corresponds to a line D.1 to D.46 of Table D.

Table 35: A compound of formula (Ib) wherein $R_1$ is 1-methyl-butyl, the bond between carbon atoms 22 and 23 is a single bond, and the combination of $R_2$ and $R_3$ for each compound corresponds to a line D.1 to D.46 of Table D.

Table 36: A compound of formula (Ib) wherein $R_1$ is 1-methyl-butyl, the bond between carbon atoms 22 and 23 is a double bond, and the combination of $R_2$ and $R_3$ for each compound corresponds to a line D.1 to D.46 of Table D.

The invention further relates to:

a process for the preparation of the compounds of formula (I) as defined above under (1) and, where applicable, tautomers thereof, which comprises:

(A) reacting a compound of formula

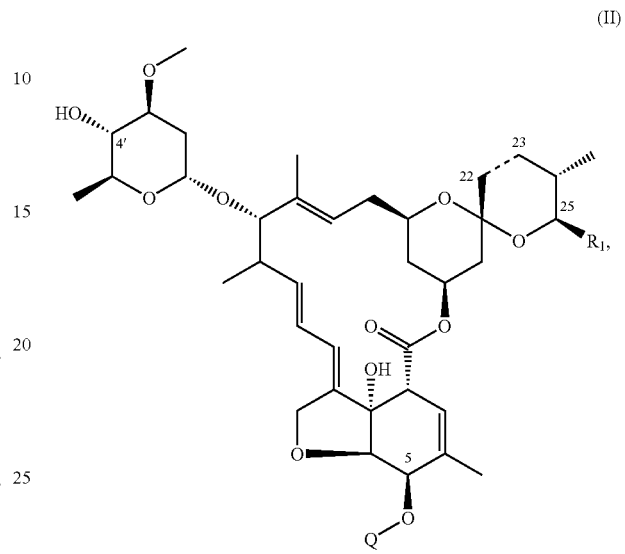

(II)

wherein the bond marked by ∼∼∼ indicates the S- as well as the R-isomer at the 4'-position; wherein $R_1$ is as defined above under (1) for formula (I), the bond between the carbon atoms 22 and 23 may be a single or a double bond;

and Q is a protecting group, and which is known or can be prepared by methods known per se, with a compound of formula

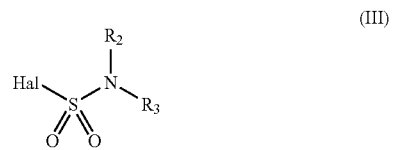

(III)

wherein $R_2$ and $R_3$ are as defined above for formula (I) and Hal is a halogen atom, preferably chlorine, bromine or iodine, and which is known or can be prepared by methods known per se, to form a compound of formula

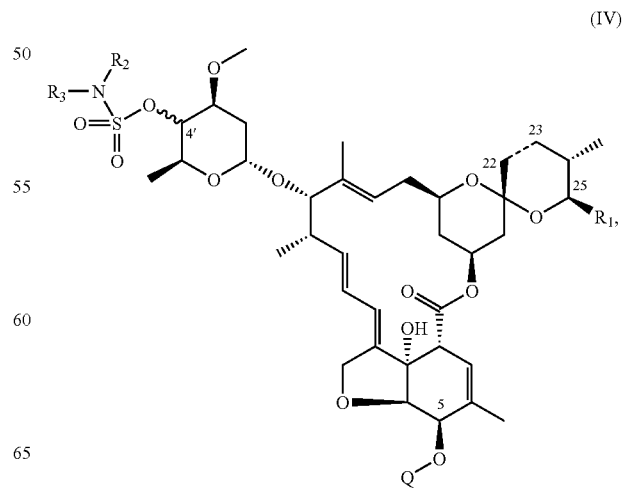

(IV)

wherein the bond between the carbon atoms 22 and 23 may be a single or a double bond; Q, $R_1$, $R_2$ and $R_3$ are as defined for formula (II); and (B) removing the protecting group Q of the compound of formula (IV) so obtained; or (C) reacting a compound of formula (I) wherein $R_1$ and $R_3$ are as defined for formula (I) and $R_2$ is H, with a compound of the formula Hal-$R_2$ wherein $R_2$ is as defined for formula (I), with exception of H, and Hal is halogen, especially chlorine, bromine or iodine; or (D) reacting a compound of formula (IV) wherein Q, $R_1$ and $R_3$ are as defined for formula (IV) and $R_2$ is H, with a compound of the formula Hal-$R_2$ wherein $R_2$ is as defined for formula (I), with exception of H, and Hal is halogen, especially chlorine, bromine or iodine; and removing the protecting group Q from the compound of formula (IV) so obtained analogously to process step (B); or a process for the preparation of a compound of formula (I) wherein $R_1$ is as defined for formula (I) and $R_2$ and $R_3$ are identical and, with the exception of hydrogen, are as defined for formula (I) and, where applicable, tautomers thereof, which comprises (E) reacting a compound of formula (I) wherein $R_1$ is as defined for formula (I) and $R_2$ and $R_3$ are H, with two moles of a compound of the formula Hal-$R_2$ wherein $R_2$ is as defined for formula (I), with exception of H, and Hal is halogen, especially chlorine, bromine or iodine; or reacting a compound of formula (IV) wherein $R_1$ is as defined for formula (IV) and $R_2$ and $R_3$ are H, with two moles of a compound of the formula Hal-$R_2$ wherein $R_2$ is as defined for formula (I), with exception of H, and Hal is halogen, especially bromine or iodine; and then removing the protecting group Q analogously to process step (B); or a process for the preparation of a compound of formula (I) wherein wherein $R_1$ is as defined for formula (I) and $R_2$ and $R_3$ together are a three- to seven-membered alkylene bridge or a four- to seven-membered alkenylene bridge wherein one $CH_2$ group in the alkylene or alkenylene may have been replaced by O, S or $NR_5$ and, where applicable, tautomers thereof, which comprises (F) reacting a compound of formula (I) wherein $R_1$ is as defined for formula (I) and $R_2$ and $R_3$ are H, with one mole of a compound of the formula Hal-A-Hal wherein the bridge member A has the above-mentioned definition of $R_2$ and $R_3$ together and Hal is halogen, especially chlorine, bromine or iodine; or, analogously to process step (E), reacting a compound of formula (IV) wherein $R_1$ and Q are as defined for formula (IV) and $R_2$ and $R_3$ are H, with one mole of a compound of the formula Hal-A-Hal as defined above, and then removing the protecting group Q analogously to process step (B); or a process for the preparation of a compound of formula (I) wherein $R_2$ is —C(O)$R_4$ and $R_1$, $R_3$ and $R_4$ are as defined for formula (I) and, where applicable, tautomers thereof, which comprises (G) either reacting a compound of formula (I) wherein $R_1$ and $R_3$ are as defined for formula (I) and $R_2$ is H, with a compound of the formula Hal-C(O)$R_4$ wherein $R_4$ is as defined above for formula (I) and Hal is halogen; or reacting a compound of formula (IV) wherein $R_1$, $R_3$, $R_4$ and Q are as defined for formula (I) and $R_2$ is H, with a compound of the formula Hal-C(O)$R_4$ wherein $R_4$ is as defined above for formula (I) and Hal is halogen; and then removing the protecting group Q.

The remarks made above regarding tautomers of compounds of formula (I) apply analogously to the starting materials mentioned hereinbefore and hereinafter with regard to their tautomers.

The reactions described hereinbefore and hereinafter are carried out in a manner known per se, for example, in the absence or, customarily, in the presence of a suitable solvent or diluent or of a mixture thereof, the reactions being carried out, as required, with cooling, at room temperature or with heating, for example, in a temperature range of approximately from $-80°$ C. to the boiling temperature of the reaction medium, preferably from approximately $0°$ C. to approximately $+150°$ C., and, if necessary, in a closed vessel, under pressure, under an inert gas atmosphere and/or under anhydrous conditions. Especially advantageous reaction conditions can be found in the Examples.

The reaction time is not critical; a reaction time of from approximately 0.1 to approximately 72 hours, especially from approximately 0.5 to approximately 24 hours, is preferred.

The product is isolated by customary methods, for example, by means of filtration, crystallisation, distillation or chromatography, or any suitable combination of such methods.

The starting materials mentioned hereinbefore and hereinafter that are used for the preparation of the compounds of formula (I) and, where applicable, their tautomers are known or can be prepared by methods known per se, e.g., as indicated below.

The starting materials of formulae

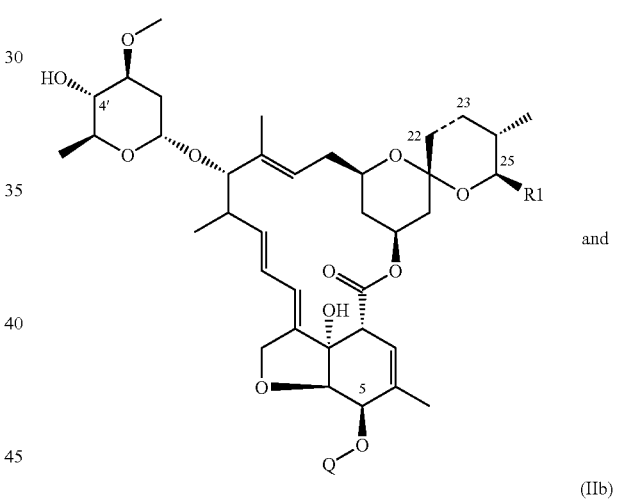

(IIa)

and

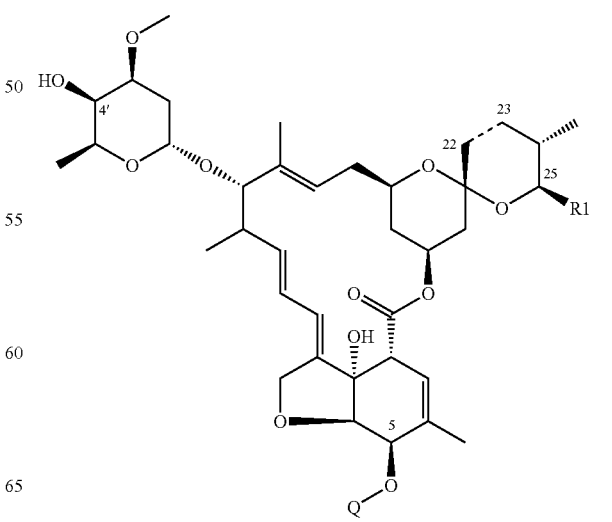

(IIb)

wherein the bond between the carbon atoms 22 and 23 may be a single or a double bond and $R_1$ and Q are as defined above formula (II) and are known to the person skilled in the art.

Process Variant (A):

Examples of solvents and diluents include: aromatic, aliphatic and alicyclic hydrocarbons and halogenated hydrocarbons, such as benzene, toluene, xylene, mesitylene, tetralin, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethyl ether, dimethoxydiethyl ether, tetrahydrofuran or dioxane; esters of carboxylic acids, such as ethyl acetate; amides, such as dimethylformamide, dimethylacetamide or 1-methyl-2-pyrrolidinones; nitriles, such as acetonitrile; sulfoxides, such as dimethyl sulfoxide; or mixtures of the mentioned solvents. Preference is given to amides, such as dimethylformamide and dimethylacetamide, especially dimethylacetamide.

Protecting groups Q in the compounds of formulae (II) and (IV) include: alkyl ether radicals, such as methoxymethyl, methylthiomethyl, tert-butylthiomethyl, benzyloxymethyl, p-methoxybenzyl, 2-methoxyethoxymethyl, 2,2,2-trichloroethoxymethyl, 2-(trimethylsilyl)ethoxymethyl, tetrahydropyranyl, tetrahydrofuranyl, 1-ethoxyethyl, 1-(2-chloroethoxy)ethyl, 1-methyl-1-methoxyethyl, 1-methyl-1-benzyloxyethyl, trichloroethyl, 2-trimethylsilylethyl, tert-butyl, allyl, p-methoxyphenyl, 2,4-dinitrophenyl, benzyl, p-methoxybenzyl, o-nitrobenzyl, p-nitrobenzyl, triphenylmethyl; trialkylsilyl radicals, such as trimethylsilyl, triethylsilyl, dimethyl-tert-butylsilyl, dimethyl-isopropylsilyl, dimethyl-1,1,2-trimethylpropylsilyl, diethyl-isopropylsilyl, dimethyl-tert-hexylsilyl, but also phenyl-tert-alkylsilyl groups, such as diphenyl-tert-butylsilyl; esters, such as formates, acetates, chloroacetates, dichloroacetates, trichloroacetates, trifluoroacetates, methoxyacetates, phenoxyacetates, pivaloates, benzoates; alkyl carbonates, such as methyl-, 9-fluorenylmethyl-, ethyl-, 2,2,2-trichloroethyl-, 2-(trimethylsilyl)ethyl-, vinyl-, allyl-, benzyl-, p-methoxybenzyl-, o-nitrobenzyl-, p-nitrobenzyl-, but also p-nitrophenyl-carbonate.

Preference is given to trialkylsilyl radicals, such as trimethylsilyl, triethylsilyl, dimethyltert-butylsilyl, diphenyl-tert-butylsilyl, esters, such as methoxyacetates and phenoxyacetates, and carbonates, such as 9-fluorenylmethylcarbonates and allylcarbonates. Dimethyl-tert-butylsilyl ether is especially preferred.

The reactions are advantageously carried out in a temperature range of from approximately −70° C. to 50° C., preferably at from −10° C. to 25° C.

Process Variant (B):

Examples of solvents and diluents are the same as those mentioned under Process variant A. In addition, alcohols, such as methanol, ethanol or 2-propanol, and water are suitable.

The reactions are advantageously carried out in a temperature range of approximately from −70° C. to 100° C., preferably at from −10° C. to 25° C.

There are suitable for the removal of the protecting group Lewis acids, such as hydrochloric acid, methanesulfonic acid, $BF_3*OEt_2$, HF in pyridine, $Zn(BF_4)_2*H_2O$, p-toluenesulfonic acid, $AlCl_3$, $HgCl_2$; ammonium fluoride, such as tetrabutylammonium fluoride; bases, such as ammonia, trialkylamine or heterocyclic bases; hydrogenolysis with a catalyst, such as palladium-on-carbon; reducing agents, such as sodium borohydride or tributyltin hydride with a catalyst, such as $Pd(PPh_3)_4$, or also zinc with acetic acid.

Preference is given to acids, such as methanesulfonic acid or HF in pyridine; sodium borohydride with Pd(0); bases, such as ammonia, triethylamine or pyridine; especially acids, such as HF in pyridine or methanesulfonic acid.

Process Variant (C):

Examples of solvents and diluents are the same as those mentioned under Process variant (A). In addition, alcohols, such as methanol, ethanol or 2-propanol, are suitable. Preference is given to amides, such as dimethylformamide, and nitriles, such as acetonitrile; especially acetonitrile.

The reactions are advantageously carried out in a temperature range of approximately from −10° C. to 120° C., preferably at from 20° C. to 100° C.

Suitable bases are especially carbonates, such as sodium carbonate, sodium hydrogen carbonate, potassium carbonate, trialkylamines, such as triethylamine, and heterocyclic bases, such as pyridine.

Process variants (D) to (F) are carried out substantially analogously to Process variant (C).

Process Variant (G):

Examples of solvents and diluents are the same as those mentioned under Process variant (B).

Ethyl acetate and water are preferred.

The reactions are advantageously carried out in a temperature range of approximately from −10° C. to 120° C., preferably at from 20° C. to 80° C.

Suitable bases are especially carbonates, such as sodium carbonate, sodium hydrogen carbonate, potassium carbonate, trialkylamines, such as triethylamine, and heterocyclic bases, such as pyridine.

The compounds of formula (I) may be in the form of one of the possible isomers or in the form of a mixture thereof, in the form of pure isomers or in the form of an isomeric mixture, i.e., in the form of a diastereomeric mixture; the invention relates both to the pure isomers and to the diastereomeric mixtures and is to be interpreted accordingly hereinabove and hereinbelow, even if stereochemical details are not mentioned specifically in every case.

The diastereomeric mixtures can be resolved into the pure isomers by known methods, for example, by recrystallisation from a solvent, by chromatography, for example, high pressure liquid chromatography (HPLC) on acetylcellulose, with the aid of suitable microorganisms, by cleavage with specific, immobilised enzymes, or via the formation of inclusion compounds, for example, using crown ethers, only one isomer being complexed.

Apart from the separation of corresponding mixtures of isomers, pure diastereoisomers can be obtained according to the invention also by generally known methods of stereoselective synthesis, for example, by carrying out the process according to the invention using starting materials having correspondingly suitable stereochemistry.

In each case it is advantageous to isolate or synthesise the biologically more active isomer, where the individual components have different biological activity.

The compounds of formula (I) may also be obtained in the form of their hydrates and/or may include other solvents, for example, solvents which may have been used for the crystallisation of compounds in solid form.

The invention relates to all those embodiments of the process according to which a compound obtainable as starting material or intermediate at any stage of the process is used as starting material and all or some of the remaining steps are carried out, or in which a starting material is used in the form of a derivative and/or a salt and/or its diastereomers, or, especially, is formed under the reaction conditions. For instance compounds of formula (I) bearing a functional group in its free or protected form can be used as starting materials for the preparation of further compounds of formula (I). For such manipulations methods known to the person skilled in the art can be applied.

In the processes of the present invention it is preferable to use those starting materials and intermediates which result in the compounds of formula (I) that are especially preferred.

The invention relates especially to the preparation processes described in the Examples.

The invention further relates to the compounds of formula (IV) and, where applicable, E/Z isomers, mixtures of E/Z isomers and/or tautomers, in each case in free form or in salt form.

In the area of pest control, the compounds of formula (I) according to the invention are active ingredients exhibiting valuable preventive and/or curative activity with a very advantageous biocidal spectrum and a very broad spectrum, even at low rates of concentration, while being well tolerated by warm-blooded animals, fish and plants. They are, surprisingly, equally suitable for controlling both plant pests and ecto- and endo-parasites in humans and more especially in productive livestock, domestic animals and pets. They are effective against all or individual development stages of normally sensitive animal pests, but also of resistant animal pests, such as insects and representatives of the order Acarina, nematodes, cestodes and trematodes, while at the same time protecting useful organisms. The insecticidal or acaricidal activity of the active ingredients according to the invention may manifest itself directly, i.e., in the mortality of the pests, which occurs immediately or only after some time, for example, during moulting, or indirectly, for example, in reduced oviposition and/or hatching rate, good activity corresponding to a mortality of at least 50 to 60%.

Successful control within the scope of the subject of the invention is possible, in particular, of pests from the orders Lepidoptera, Coleoptera, Orthoptera, Isoptera, Psocoptera, Anoplura, Mallophaga, Thysanoptera, Heteroptera, Homoptera, Hymenoptera, Diptera, Siphonaptera, Thysanura and Acarina, mainly Acarina, Diptera, Thysanoptera, Lepidoptera and Coleoptera. Very especially good control is possible of the following pests:

*Abagrotis* spp., *Abraxas* spp., *Acantholeucania* spp., *Acanthoplusia* spp., *Acarus* spp., *Acarus siro*, *Aceria* spp., *Aceria sheldoni*, *Acleris* spp., *Acoloithus* spp., *Acompsia* spp., *Acossus* spp., *Acria* spp., *Acrobasis* spp., *Acrocercops* spp., *Acrolepia* spp., *Acrolepiopsis* spp., *Acronicta* spp., *Acropolitis* spp., *Actebia* spp., *Aculus* spp., *Aculus schlechtendali*, *Adoxophyes* spp., *Adoxophyes reticulana*, *Aedes* spp., *Aegeria* spp., *Aethes* spp., *Agapeta* spp., *Agonopterix* spp., *Agriopis* spp., *Agriotes* spp., *Agriphila* spp., *Agrochola* spp., *Agroperina* spp., *Alabama* ssp., *Alabama argillaceae*, *Agrotis* spp., *Albuna* spp., *Alcathoe* spp., *Alcis* spp., *Aleimma* spp., *Aletia* spp., *Aleurothrixus* spp., *Aleurothrixus floccosus*, *Aleyrodes* spp., *Aleyrodes brassicae*, *Allophyes* spp., *Alsophila* spp., *Amata* spp., *Amathes* spp., *Amblyomma* spp., *Amblyptilia* spp., *Ammoconia* spp., *Amorbia* spp., *Amphion* spp., *Amphipoea* spp., *Amphipyra* spp., *Amyelois* spp., *Anacamptodes* spp., *Anagrapha* spp., *Anarsia* spp., *Anatrychyntis* spp., *Anavitrinella* spp., *Ancylis* spp., *Andropolia* spp., *Anhimella* spp., *Antheraea* spp., *Antherigona* spp., *Antherigona soccata*, *Anthonomus* ssp., *Anthonomus grandis*, *Anticarsia* spp., *Anticarsia gemmatalis*, *Aonidiella* spp., *Apamea* spp., *Aphania* spp., *Aphelia* spp., Aphididae, *Aphis* spp., *Apotomis* spp., *Aproaerema* spp., *Archippus* spp., *Archips* spp., *Acromyrmex*, *Arctia* spp., *Argas* spp., *Argolamprotes* spp., *Argyresthia* spp., *Argyrogramma* spp., *Argyroploce* spp., *Argyrotaenia* spp., *Arotrophora* spp., *Ascotis* spp., *Aspidiotus* spp., *Aspilapteryx* spp., *Asthenoptycha* spp., *Aterpia* spp., *Athetis* spp., *Atomaria* spp., *Atomaria linearis*, *Afta* spp., *Atypha* spp., *Autographa* spp., *Axylia* spp., *Bactra* spp., *Barbara* spp., *Batrachedra* spp., *Battaristis* spp., *Bembecia* spp., *Bemisia* spp., *Bemisia tabaci*, *Bibio* spp., *Bibio hortulanis*, *Bisigna* spp., *Blastesthia* spp., *Blatta* spp., *Blatella* spp., *Blepharosis* spp., *Bleptina* spp., *Boarmia* spp., *Bombyx* spp., *Bomolocha* spp., *Boophilus* spp., *Brachmia* spp., *Bradina* spp., *Brevipalpus* spp., *Brithys* spp., *Bryobia* spp., *Bryobia praetiosa*, *Bryotropha* spp., *Bupalus* spp., *Busseola* spp., *Busseola fusca*, *Cabera* spp., *Cacoecimorpha* spp., *Cadra* spp., *Cadra cautella*, *Caenurgina* spp., *Calipitrimerus* spp., *Callierges* spp., *Callophpora* spp., *Callophpora erythrocephala*, *Calophasia* spp., *Caloptilia* spp., *Calybites* spp., *Capnoptycha* spp., *Capua* spp., *Caradrina* spp., *Caripeta* spp., *Carmenta* spp., *Carposina* spp., *Carposina nipponensis*, *Catamacta* spp., *Catelaphris* spp., *Catoptria* spp., *Caustoloma* spp., *Celaena* spp., *Celypha* spp., *Cenopis* spp., *Cephus* spp., *Ceramica* spp., *Cerapteryx* spp., *Ceratitis* spp, *Ceratophyllus* spp., *Ceroplaster* spp., *Chaetocnema* spp., *Chaetocnema tibialis*, *Chamaesphecia* spp., *Charanvca* spp., *Cheimophila* spp., *Chersotis* spp., *Chiasmia* spp., *Chilo* spp., *Chionodes* spp., *Chorioptes* spp., *Choristoneura* spp., *Chrysaspidia* spp., *Chrysodeixis* spp., *Chrysomya* spp., *Chrysomphalus* spp., *Chrysomphalus dictyospermi*, *Chrysomphalus aorlidium*, *Chrysoteuchia* spp., *Cilix* spp., *Cimex* spp., *Clysia* spp., *Clysia ambiguella*, *Clepsis* spp., *Cnaemidophorus* spp., *Cnaphalocrocis* spp., *Cnephasia* spp., *Coccus* spp., *Coccus hesperidum*, *Cochylis* spp., *Coleophora* spp., *Colotois* spp., *Commophila* spp., *Conistra* spp., *Conopomorpha* spp., *Corcyra* spp., *Cornutiplusia* spp., *Cosmia* spp., *Cosmopolites* spp., *Cosmopterix* spp., *Cossus* spp., *Costaeonvexa* spp., *Crambus* spp., *Creatonotos* spp., *Crocidolomia* spp., *Crocidolomia binotalis*, *Croesia* spp., *Crymodes* spp., *Cryptaspasma* spp., *Cryptoblabes* spp., *Cryptocala* spp., *Cryptophlebia* spp., *Cryptophlebia leucotreta*, *Cryptoptila* spp., *Ctenopseustis* spp., *Cucullia* spp., *Curculio* spp., *Culex* spp., *Cuterebra* spp., *Cydia* spp., *Cydia pomonella*, *Cymbalophora* spp., *Dactylethra* spp., *Dacus* spp., *Dadica* spp., *Damalinea* spp., *Dasychira* spp., *Decadarchis* spp., *Decodes* spp., *Deilephila* spp., *Deltodes* spp., *Dendrolimus* spp., *Depressaria* spp., *Dermestes* spp., *Dermanyssus* spp., *Dermanyssus gallinae*, *Diabrotica* spp., *Diachrysia* spp., *Diaphania* spp., *Diarsia* spp., *Diasemia* spp., *Diatraea* spp., *Diceratura* spp., Dichomeris spp., *Dichrocrocis* spp., *Dichrorampha* spp., *Dicycla* spp., *Dioryctria* spp., *Diparopsis* spp., *Diparopsis castanea*, *Dipleurina* spp., *Diprion* spp., *Diprionidae*, *Discestra* spp., *Distantiella* spp., *Distantiella theobroma*, *Ditula* spp., *Diumea* spp., *Doratopteryx* spp., *Drepana* spp., *Drosphila* spp., *Drosphila melanogaster*, *Dysauxes* spp., *Dysdercus* spp., *Dysstroma* spp., *Eana* spp., *Earias* spp., *Ecclitica* spp., *Ecdytolopha* spp., *Ecpyrrhorrhoe* spp., *Ectomyelois* spp., *Eetropis* spp., *Egira* spp., *Elasmopalpus* spp., *Emmelia* spp., *mpoasca* spp., *Empyreuma* spp., *Enargia* spp., *Enarmonia* spp., *Endopiza* spp., *Endothenia* spp., *Endotricha* spp., *Eoreuma* spp., *Eotetranychus* spp., *Eotetranychus carpini*, *Epagoge* spp., *Epelis* spp., *Ephestia* spp., *Ephestiodes* spp., *Epiblema* spp., *Epiehoristodes* spp., *Epinotia* spp., *Epiphyas* spp., *Epiplema* spp., *Epipsestis* spp., *Epirrhoe* spp., *Episimus* spp., *Epitymbia* spp., *Epilachna* spp., *Erannis* spp., *Erastria* spp., *Eremnus* spp., *Ereunetis* spp., *Eriophyes* spp., *Eriosoma* spp., *Eriosoma lanigerum*, *Erythroneura* spp., *Estigmene* spp., *Ethmia* spp., *Etiella* spp., *Euagrotis* spp., *Eucosma* spp., *Euehlaena* spp., *Euelidia* spp., *Eueosma* spp., *Euchistus* spp., *Eucosmomorpha* spp.,

*Eudonia* spp., *Eufidonia* spp., *Euhyponomeutoides* spp., *Eulepitodes* spp., *Eulia* spp., *Eulithis* spp., *Eupithecia* spp., *Euplexia* spp., *Eupoecilia* spp., *Eupoecilia ambiguella*, *Euproctis* spp., *Eupsilia* spp., *Eurhodope* spp., *Eurois* spp., *Eurygaster* spp., *Eurythmia* spp., *Eustrotia* spp., *Euxoa* spp., *Euzophera* spp., *Evergestis* spp., *Evippe* spp., *Exartema* spp., *Fannia* spp., *Faronta* spp., *Feltia* spp., *Filatima* spp., *Fishia* spp., *Frankliniella* spp., *Fumibotys* spp., *Gaesa* spp., *Gasgardia* spp., *Gastrophilus* spp., *Gelechia* spp., *Gilpinia* spp., *Gilpinia polytoma*, *Glossina* spp., *Glyphipterix* spp., *Glyphodes* spp., *Gnorimoschemini* spp., *Gonodonta* spp., *Gortyna* spp., *Gracillaria* spp., *Graphania* spp., *Grapholita* spp., *Grapholitha* spp., *Gravitarmata* spp., *Gretchena* spp., *Griselda* spp., *Gryllotalpa* spp., *Gynaephora* spp., *Gypsonoma* spp., *Hada* spp., *Haematopinus* spp., *Halisidota* spp., *Harpipteryx* spp., *Harrisina* spp., *Hedya* spp., *Helicoverpa* spp., *Heliophobus* spp., *Heliothis* spp., *Hellula* spp., *Helotropa* spp., *Hemaris* spp., *Hercinothrips* spp., *Herculia* spp., *Hermonassa* spp., *Heterogenea* spp., *Holomelina* spp., *Homadaula* spp., *Homoeosoma* spp., *Homoglaea* spp., *Homohadena* spp., *Homona* spp., *Homonopsis* spp., *Hoplocampa* spp., *Hoplodrina* spp., *Hoshinoa* spp., *Hxalomma* spp., *Hydraecia* spp., *Hydriomena* spp., *Hyles* spp., *Hyloicus* spp., *Hypagyrtis* spp., *Hypatima* spp., *Hyphantria* spp., *Hyphantria* cunea, *Hypocala* spp., *Hypocoena* spp., *Hypodema* spp., *Hyppobosca* spp., *Hypsipyla* spp., *Hyssia* spp., *Hysterosia* spp., *Idaea* spp., *Idia* spp., *Ipimorpha* spp., *Isia* spp., *Isochorista* spp., *Isophrictis* spp., *Isopolia* spp., *Isotrias* spp., *Ixodes* spp., *Itame* spp., *Jodia* spp., *Jodis* spp., *Kawabea* spp., *Keiferia* spp., *Keiferia lycopersicella*, *Labdia* spp., *Lacinipolia* spp., *Lambdina* spp., *Lamprothritpa* spp., *Laodelphax* spp., *Lasius* spp., *Laspeyresia* spp., *Leptinotarsa* spp., *Leptinotarsa decemlineata*, *Leptocorisa* spp., *Leptostales* spp., *Lecanium* spp., *Lecanium corni*, *Lepidosaphes* spp., *Lepisma* spp., *Lepisma saccharina*, *Lesmone* spp., *Leucania* spp., *Leucinodes* spp., *Leucophaea* spp., *Leucophaea maderae*, *Leucoptera* spp., *Leucoptera scitella*, *Linognathus* spp., *Uposcelis* spp., *Lissorhoptrus* spp., *Lithacodia* spp., *Lithocolletis* spp., *Lithomoia* spp., *Lithophane* spp., *Lixodessa* spp., *Lobesia* spp., *Lobesia botrana*, *Lobophora* spp., *Locusta* spp., *Lomanaltes* spp., *Lomographa* spp., *Loxagrotis* spp., *Loxostege* spp., *Lucilia* spp., *Lymantria* spp., *Lymnaecia* spp., *Lyonetia* spp., *Lyriomyza* spp., *Macdonnoughia* spp., *Macrauzata* spp., *Macronoctua* spp., *Macrosiphus* spp., *Malacosoma* spp., *Maliarpha* spp., *Mamestra* spp., *Mamestra brassicae*, *Manduca* spp., *Manduca sexta*, *Marasmia* spp., *Margaritia* spp., *Matratinea* spp., *Matsumuraeses* spp., *Melanagromyza* spp., *Melipotes* spp., *Melissopus* spp., *Melittia* spp., *Melolontha* spp., *Meristis* spp., *Meritastis* spp., *Merophyas* spp., *Mesapamea* spp., *Mesogona* spp., *Mesoleuca* spp., *Metanema* spp., *Metendothenia* spp., *Metzneria* spp., *Micardia* spp., *Microcorses* spp., *Microleon* spp., *Mnesictena* spp., *Mocis* spp., *Monima* spp., *Monochroa* spp., *Monomorium* spp., *Monomorium pharaonis*, *Monopsis* spp., *Morrisonia* spp., *Musca* spp., *Mutuuraia* spp., *Myelois* spp., *Mythimna* spp., *Myzus* spp., *Naranga* spp., *Nedra* spp., *Nemapogon* spp., *Neodiprion* spp., *Neosphaleroptera* spp., *Nephelodes* spp., *Nephotettix* spp., *Nezara* spp., *Nilaparvata* spp., *Niphonympha* spp., *Nippoptilia* spp., *Noctua* spp., *Nola* spp., *Notocelia* spp., *Notodonta* spp., *Nudaurelia* spp., *Ochropleura* spp., *Ocnerostoma* spp., *Oestrus* spp., *Olethreutes* spp., *Oligia* spp., *Olindia* spp., *Olygonychus* spp., *Olygonychus gallinae*, *Oncocnemis* spp., *Operophtera* spp., *Ophisma* spp., *Opogona* spp., *Oraesia* spp., *Orniodoros* spp., *Orgyia* spp., *Oria* spp., *Orseolia* spp., *Orthodes* spp., *Orthogonia* spp., *Orthosia* spp., *Oryzaephilus* spp., *Oscinella* spp., *Oscinella frit*, *Osminia* spp., *Ostrinia* spp., *Ostrinia nubilalis*, *Otiorhynchus* spp., *Ourapteryx* spp., *Pachetra* spp., *Pachysphinx* spp., *Pagyda* spp., *Paleacrita* spp., *Paliga* spp., *Palthis* spp., *Pammene* spp., *Pandemis* spp., *Panemeria* spp., *Panolis* spp., *Panolis flammea*, *Panonychus* spp., *Parargyresthia* spp., *Paradiarsia* spp., *Paralobesia* spp., *Paranthrene* spp., *Parapandemis* spp., *Parapediasia* spp., *Parastichtis* spp., *Parasyndemis* spp., *Paratoria* spp., *Pareromeme* spp., *Pectinophora* spp., *Pectinophora gossypiella*, *Pediculus* spp., *Pegomyia* spp., *Pegomyia hyoscyami*, *Pelochrista* spp., *Pennisetia* spp., *Penstemonia* spp., *Pemphigus* spp., *Peribatodes* spp., *Peridroma* spp., *Perileucoptera* spp., *Periplaneta* spp., *Perizoma* spp., *Petrova* spp., *Pexicopia* spp., *Phalonia* spp., *Phalonidia* spp., *Phaneta* spp., *Phlyctaenia* spp., *Phlyctinus* spp., *Phorbia* spp., *Phragmatobia* spp., *Phricanthes* spp., *Phthorimaea* spp., *Phthorimaea operculella*, *Phyllocnistis* spp., *Phyllocoptruta* spp., *Phyllocoptruta oleivora*, *Phyllonorycter* spp., *Phyllophila* spp., *Phylloxera* spp., *Pieris* spp., *Pieris rapae*, *Piesma* spp., *Planococus* spp., *Planotortrix* spp., *Platyedra* spp., *Platynota* spp., *Platyptilia* spp., *Platysenta* spp., *Plodia* spp., *Plusia* spp., *Plutella* spp., *Plutella xylostella*, *Podosesia* spp., *Polia* spp., *Popillia* spp., *Polymixis* spp., *Polyphagotarsonemus* spp., *Polyphagotarsonemus latus*, *Prays* spp., *Prionoxystus* spp., *Probole* spp., *Proceras* spp., *Prochoerodes* spp., *Proeulia* spp., *Proschistis* spp., *Proselena* spp., *Proserpinus* spp., *Protagrotis* spp., *Proteoteras* spp., *Protobathra* spp., *Protoschinia* spp., *Pselnophorus* spp., *Pseudaletia* spp., *Pseudanthonomus* spp., *Pseudaternelia* spp., *Pseudaulacaspis* spp., *Pseudexentera* spp., *Pseudococus* spp., *Pseudohermenias* spp., *Pseudoplusia* spp., *Psoroptes* spp., *Psylla* spp., *Psylliodes* spp., *Pterophorus* spp., *Ptycholoma* spp., *Pulvinaria* spp., *Pulvinaria aethiopica*, *Pyralis* spp., *Pyrausta* spp., *Pyrgotis* spp., *Pyrreferra* spp., *Pyrrharctia* spp., *Quadraspidiotus* spp., *Rancora* spp., *Raphia* spp., *Reticultermes* spp., *Retinia* spp., *Rhagoletis* spp., *Rhagoletis pomonella*, *Rhipicephalus* spp., *Rhizoglyphus* spp., *Rhizopertha* spp., *Rhodnius* spp., *Rhophalosiphum* spp., *Rhopobota* spp., *Rhyacia* spp., *Rhyacionia* spp., *Rhynchopacha* spp., *Rhyzosthenes* spp., *Rivula* spp., *Rondotia* spp., *Rusidrina* spp., *Rynchaglaea* spp., *Sabulodes* spp., *Sahlbergella* spp., *Sahlbergella singularis*, *Saissetia* spp., *Samia* spp., *Sannina* spp., *Sanninoidea* spp., *Saphoideus* spp., *Sarcoptes* spp., *Sathrobrota* spp., *Scarabeidae*, *Sceliodes* spp., *Schinia* spp., *Schistocerca* spp., *Schizaphis* spp., *Schizura* spp., *Schreckensteinia* spp., *Sciara* spp., *Scirpophaga* spp., *Scirthrips auranti*, *Scoparia* spp., *Scopula* spp., *Scotia* spp., *Scotinophara* spp., *Scotogramma* spp., *Scrobipalpa* spp., *Scrobipalpopsis* spp., *Semiothisa* spp., *Sereda* spp., *Sesamia* spp., *Sesia* spp., *Sicya* spp., *Sideridis* spp., *Simyra* spp., *Sineugraphe* spp., *Sitochroa* spp., *Sitobion* spp., *Sitophilus* spp., *Sitotroga* spp., *Solenopsis* spp., *Smerinthus* spp., *Sophronia* spp., *Spaelotis* spp., *Spargaloma* spp., *Sparganothis* spp., *Spatalistis* spp., *Sperchia* spp., *Sphecia* spp., *Sphinx* spp., *Spilonota* spp., *Spodoptera* spp., *Spodoptera littoralis*, *Stagmatophora* spp., *Staphylinochrous* spp., *Stathmopoda* spp., *Stenodes* spp., *Sterrha* spp., *Stomoxys* spp., *Strophedra* spp., *Sunira* spp., *Sutyna* spp., *Swammerdamia* spp., *Syllomatia* spp., *Sympistis* spp., *Synanthedon* spp., *Synaxis* spp., *Syncopacma* spp., *Syndemis* spp., *Syngrapha* spp., *Synthomeida* spp., *Tabanus* spp., *Taeniarchis* spp., *Taeniothrips* spp., *Tannia* spp., *Tarsonemus* spp., *Tegulifera* spp., *Tehama* spp., *Telejodes* spp., *Telorta* spp., *Tenebrio* spp., *Tephrina* spp., *Teratoglaea* spp., *Terricula* spp., *Tethea* spp., *Tetranychus* spp., *Thalpophila* spp., *Thaumetopoea* spp., *Thiodia* spp., *Thrips* spp., *Thrips palmi*, *Thrips tabaci*, *Thyridopteryx* spp., *Thyris* spp., *Tineola* spp., *Tipula* spp., *Tortricidia* spp., *Tortrix* spp., *Trachea* spp., *Trialeurodes* spp., *Trialeurodes vaporariorum*, *Triatoma* spp., *Triaxomera* spp., *Tribolium* spp., *Tricodectes* spp., *Trichoplusia* spp., *Trichoplusia ni*, *Trichoptilus* spp., *Trioza* spp., *Trioza erytreae*, *Triphaenia* spp., *Triphosa* spp., *Trogoderma* spp., *Tyria* spp., *Udea* spp., *Unaspis* spp., *Unaspis* citri, *Utetheisa* spp., *Valeriodes* spp., *Vespa* spp., *Vespamima* spp., *Vitacea* spp., *Vitula* spp., *Witlesia* spp., *Xanthia* spp., *Xanthorhoe* spp., *Xanthotype* spp., *Xenomicta* spp., *Xenopsylla* spp., *Xenopsylla* cheopsis, *Xestia* spp., *Xylena* spp., *Xylomyges* spp., *Xyrosaris* spp., *Yponomeuta* spp., *Ypsolopha* spp., *Zale* spp., *Zanclognathus* spp., *Zeiraphera* spp., *Zenodoxus* spp., *Zeuzera* spp., *Zygaena* spp., It is also possible to control pests of the class Nematoda using the compounds according to the invention. Such pests include, for example, root knot nematodes, cyst-forming nematodes and also stem and leaf nematodes;

especially of *Heterodera* spp., e.g., *Heterodera schachtii*, *Heterodora avenae* and *Heterodora trifolii*; *Globodera* spp., e.g., *Globodera rostochiensis*; *Meloidogyne* spp., e.g., *Meloidogyne incognita* and *Meloidogyne javanica*; *Radopholus* spp., e.g., *Radopholus similis*; *Pratylenchus*, e.g., *Pratylenchus neglectans* and *Pratylenchus penetrans*; *Tylenchulus*, e.g., *Tylenchulus semipenetrans*; *Longidorus*, *Trichodorus*, *Xiphinema*, *Ditylenchus*, *Apheenchoides* and *Anguina*; especially *Meloidogyne*, e.g., *Meloidogyne incognita*, and *Heterodera*, e.g., *Heterodera glycines*.

An especially important aspect of the present invention is the use of the compounds of formula (I) according to the invention in the protection of plants against parasitic feeding pests.

The action of the compounds according to the invention and the compositions comprising them against animal pests can be significantly broadened and adapted to the given circumstances by the addition of other insecticides, acaricides or nematicides. Suitable additives include, for example, representatives of the following classes of active ingredient: organophosphorus compounds, nitrophenols and derivatives, formamidines, ureas, carbamates, pyrethroids, chlorinated hydrocarbons, neonicotinoids and *Bacillus thuringiensis* preparations.

Examples of especially suitable mixing partners include: azamethiphos; chlorfenvinphos; cypermethrin, cypermethrin high-cis; cyromazine; diafenthiuron; diazinon; dichlorvos; dicrotophos; dicyclanil; fenoxycarb; fluazuron; furathiocarb; isazofos; iodfenphos; kinoprene; lufenuron; methacriphos; methidathion; monocrotophos; phosphamidon; profenofos; diofenolan; a compound obtainable from the *Bacillus thuringiensis* strain GC91 or from strain NCTC11821; pymetrozine; bromopropylate; methoprene; disulfoton; quinalphos; taufluvalinate; thiocyclam; thiometon; aldicarb; azinphos-methyl; benfuracarb; bifenthrin; buprofezin; carbofuran; dibutylaminothio; cartap; chlorfluazuron; chlorpyrifos; clothianidin; cyfluthrin; lambda-cyhalothrin; alpha-cypermethrin; zeta-cypermethrin; deltamethrin; diflubenzuron; endosulfan; ethiofencarb; fenitrothion; fenobucarb; fenvalerate; formothion; methiocarb; heptenophos; imidacloprid; isoprocarb; methamidophos; methomyl; mevinphos; parathion; parathion-methyl; phosalone; pirimicarb; propoxur; teflubenzuron; terbufos; triazamate; fenobucarb; tebufenozide; fipronil; beta-cyfluthrin; silafluofen; fenpyroximate; pyridaben; fenazaquin; pyriproxyfen; pyrimidifen; nitenpyram; acetamiprid; emamectin; emamectin-benzoate; spinosad; a plant extract that is active against insects; a preparation that comprises nematodes and is active against insects; a preparation obtainable from *Bacillus subtilis*; a preparation that comprises fungi and is active against insects; a preparation that comprises viruses and is active against insects; chlorfenapyr; acephate; acrinathrin; alanycarb; alphamethrin; amitraz; AZ 60541; azinphos A; azinphos M; azocyclotin; bendiocarb; bensultap; beta-cyfluthrin; BPMC; brofenprox; bromophos A; bufencarb; butocarboxin; butylpyridaben; cadusafos; carbaryl; carbophenothion; chloethocarb; chlorethoxyfos; chlormephos; cis-resmethrin; clocythrin; clofentezine; cyanophos; cycloprothrin; cyhexatin; demeton M; demeton S; demeton-S-methyl; dichlofenthion; dicliphos; diethion; dimethoate; dimethylvinphos; dioxathion; edifenphos; esfenvalerate; ethion; ethotenprox; ethoprophos; etrimphos; fenamiphos; fenbutatin oxide; fenothiocarb; fenpropathrin; fenpyrad; fenthion; fluazinam; flucycloxuron; flucythrinate; flufenoxuron; flufenprox; fonophos; fosthiazate; fubfenprox; HCH; hexaflumuron; hexythiazox; IKI-220; iprobenfos; isofenphos; isoxathion; ivermectin; malathion; mecarbam; mesulfenphos; metaldehyde; metolcarb; milbemectin; moxidectin; naled; NC 184; nithiazine; omethoate; oxamyl; oxydemethon M; oxydeprofos; permethrin; phenthoate; phorate; phosmet; phoxim; pirimiphos M; pirimiphos E; promecarb; propaphos; prothiofos; prothoate; pyrachlophos; pyradaphenthion; pyresmethrin; pyrethrum; tebufenozide; salithion; sebufos; sulfotep; sulprofos; tebufenpyrad; tebupirimphos; tefluthrin; temephos; terbam; tetrachlorvinphos; thiacloprid; thiafenox; thiamethoxam; thiodicarb; thiofanox; thionazin; thuringiensin; tralomethrin; triarathene; triazophos; triazuron; trichlorfon; triflumuron; trimethacarb; vamidothion; xylylcarb; YI 5301/5302; zetamethrin; DPX-MP062—indoxacarb; methoxyfenozide; bifenazate; XMC (3,5-xylyl methylcarbamate); or the fungus pathogen *Metarhizium* anisopliae.

The compounds according to the invention can be used to control, i.e., to inhibit or destroy, pests of the mentioned type occurring on plants, especially on useful plants and ornamentals in agriculture, in horticulture and in forestry, or on parts of such plants, such as the fruits, blossoms, leaves, stems, tubers or roots, while in some cases plant parts that grow later are still protected against those pests.

Target crops include especially cereals, such as wheat, barley, rye, oats, rice, maize and sorghum; beet, such as sugar beet and fodder beet; fruit, e.g., pomes, stone fruit and soft fruit, such as apples, pears, plums, peaches, almonds, cherries and berries, e.g., strawberries, raspberries and blackberries; leguminous plants, such as beans, lentils, peas and soybeans; oil plants, such as rape, mustard, poppy, olives, sunflowers, coconut, castor oil, cocoa and groundnuts; cucurbitaceae, such as marrows, pepper, eggplants, cucumbers and melons; fibre plants, such as cotton, flax, hemp and jute; citrus fruits, such as oranges, lemons, grapefruit and mandarins; vegetables, such as spinach, lettuce, asparagus, cabbages, carrots, onions, tomatoes, potatoes and paprika; lauraceae, such as avocado, cinnamon and camphor; tobacco; nuts; coffee; sugar cane; tea; vines; hops; bananas, natural rubber plants; and ornamentals.

The invention therefore relates also to a pesticidal composition, such as emulsifiable concentrates, suspension concentrates, directly sprayable or dilutable solutions, spreadable pastes, dilute emulsions, wettable powders, soluble powders, dispersible powders, wettable powders, dusts, granules and encapsulations of polymer substances, that comprises at least one compound of formula (I), the choice of formulation being made in accordance with the intended objectives and the prevailing circumstances. Furthermore, the pesticidal composition is often diluted, and optionally combined with other pesticidal compositions, before its use as a pesticide. The invention, therefore, also relates to a tank mix composition (sometimes referred to as a slurry in the event the composition is a suspension), which comprises the pesticidal composition and a liquid carrier, generally water, and optionally one or more other pesticidal compositions, each other pesticidal composition comprising a further pesticide as active compound.

The active ingredient is used in those compositions in pure form, a solid active ingredient, for example, in a specific particle size, or preferably together with at least one of the auxiliary (also known as adjuvants) customary in formulation technology, such as extenders, e.g., solvents or solid carriers, or surface-active compounds (surfactants). In the area of parasite control in humans, domestic animals, productive livestock and pets it will be self-evident that only physiologically tolerable additives are used.

Solvents are, for example: non-hydrogenated or partly hydrogenated aromatic hydrocarbons, preferably fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols, such as ethanol, propanol or butanol, glycols and ethers and esters thereof, such as propylene glycol, dipropylene glycol ether, ethylene glycol or ethylene glycol monomethyl or -ethyl ether, ketones, such as cyclohexanone, isophorone or diacetone alcohol, strongly polar solvents, such as N-methylpyrrolid-2-one, dimethyl sulfoxide or N,N-dimethylformamide, water, non-epoxidized or epoxidized plant oils, such as non-epoxidized or epoxidized rapeseed, castor, coconut or soya oil, and silicone oils.

The solid carriers used, for example, for dusts and dispersible powders, are as a rule natural rock powders, such as calcite, talc, kaolin, montmorillonite or attapulgite. Highly disperse silicic acids or highly disperse absorbent polymers can also be added to improve the physical properties. Granular adsorptive granule carriers are porous types, such as pumice, crushed brick, sepiolite or bentonite, and non-sorbent carrier materials are calcite or sand. A large number of granular materials of inorganic or organic nature can furthermore be used, in particular dolomite or comminuted plant residues.

Surface-active compounds are, depending on the nature of the active compound to be formulated, nonionic, cationic and/or anionic surfactants or surfactant mixtures with good emulsifying, dispersing and wetting properties. The surfactants listed below are to be regarded only as examples; many other surfactants that are customary in formulation technology are suitable and are described in the relevant literature.

Nonionic surfactants are, in particular, polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl radical of the alkylphenols. Substances which are furthermore suitable are water-soluble polyethylene oxide adducts, containing 20 to 250 ethylene glycol ether and 10 to 100 propylene glycol ether groups, on propylene glycol, ethylene diaminopolypropylene glycol and alkyl polypropylene glycol having 1 to 10 carbon atoms in the alkyl chain. The compounds mentioned usually contain 1 to 5 ethylene glycol units per propylene glycol unit. Examples are nonylphenol-polyethoxyethanols, castor oil polyglycol ethers, polypropylene-polyethylene oxide adducts, tributylphenoxypoly-ethoxyethanol, polyethylene glycol and octylphenoxypolyethoxyethanol. Other substances are fatty acid esters of polyoxyethylene sorbitan, such as polyoxyethylene sorbitan trioleate.

The cationic surfactants are, in particular, quaternary ammonium salts which contain, as substituents, at least one alkyl radical having 8 to 22 C atoms and, as further substituents, lower, non-halogenated or halogenated alkyl, benzyl or lower hydroxyalkyl radicals. The salts are preferably in the form of halides, methyl-sulfates or ethyl-sulfates. Examples are stearyl-trimethyl-ammonium chloride and benzyl-di-(2-chloroethyl)-ethylammonium bromide.

Suitable anionic surfactants can be both water-soluble soaps and water-soluble synthetic surface-active compounds. Suitable soaps are the alkali metal, alkaline earth metal and substituted or unsubstituted ammonium salts of higher fatty acids ($C_{10}$-$C_{22}$), such as the sodium or potassium salts of oleic or stearic acid, or of naturally occurring fatty acid mixtures, which can be obtained, for example, from coconut oil or tall oil; and furthermore also the fatty acid methyl-taurine salts. However, synthetic surfactants are more frequently used, in particular fatty sulfonates, fatty sulfates, sulfonated benzimidazole derivatives or alkylarylsulfonates. The fatty sulfonates and sulfates are as a rule in the form of alkali metal, alkaline earth metal or substituted or unsubstituted ammonium salts and in general have an alkyl radical of 8 to 22 C atoms, alkyl also including the alkyl moiety of acyl radicals; examples are the sodium or calcium salt of ligninsulfonic acid, of dodecyl-sulfuric acid ester or of a fatty alcohol sulfate mixture prepared from naturally occurring fatty acids. These also include the salts of sulfuric acid esters and sulfonic acids of fatty alcohol-ethylene oxide adducts. The sulfonated benzimidazole derivatives preferably contain 2 sulfonic acid groups and a fatty acid radical having about 8 to 22 C atoms. Alkylarylsulfonates are, for example, the sodium, calcium or triethanolammonium salts of dodecylbenzenesulfonic acid, of dibutyinaphthalenesulfonic acid or of a naphthalenesulfonic acid-formaldehyde condensation product. Corresponding phosphates, such as salts of the phosphoric acid ester of a p-nonylphenol-(4-14)-ethylene oxide adduct or phospholipids, can further also be used.

The compositions as a rule comprise 0.1 to 99%, in particular 0.1 to 95%, of active compound and 1 to 99.9%, in particular 5 to 99.9%, of at least one solid or liquid auxiliary, it being possible as a rule for 0 to 25%, in particular 0.1 to 20%, of the composition to be surfactants (% is in each case percent by weight). While concentrated compositions are more preferred as commercial goods, the end user as a rule uses dilute compositions which comprise considerably lower concentrations of active compound. Preferred compositions are composed, in particular, as follows (%=percent by weight):

Emulsifiable Concentrates:

| | |
|---|---|
| active ingredient: | 1 to 90%, preferably 5 to 20% |
| surfactant: | 1 to 30%, preferably 10 to 20% |
| solvent: | balance |

Dusts:

| | |
|---|---|
| active ingredient: | 0.1 to 10%, preferably 0.1 to 1% |
| solid carrier: | 99.9 to 90%, preferably 99.9 to 99% |

Suspension Concentrates:

| | |
|---|---|
| active ingredient: | 5 to 75%, preferably 10 to 50% |
| surfactant: | 1 to 40%, preferably 2 to 30% |
| water: | balance |

Wettable Powders:

| | |
|---|---|
| active ingredient: | 0.5 to 90%, preferably 1 to 80% |
| surfactant: | 0.5 to 20%, preferably 1 to 15% |
| solid carrier: | balance |

Granules:

| | |
|---|---|
| active ingredient: | 0.5 to 30%, preferably 3 to 15% |
| solid carrier: | 99.5 to 70%, preferably 97 to 85% |

Specific formulation examples for use in crop protection are given below (%=percent by weight):

EXAMPLE F1

Emulsifiable Concentrates

| | a) | b) | c) |
|---|---|---|---|
| Active compound | 25% | 40% | 50% |
| Calcium dodecylbenzenesulphonate | 5% | 8% | 6% |
| Castor oil polyethylene glycol ether (36 mol of EO) | 5% | — | — |
| Tributylphenol polyethylene glycol ether (30 mol of EO) | — | 12% | 4% |
| Cyclohexanone | — | 15% | 20% |
| Xylene mixture | 65% | 25% | 20% |

Mixing of finely ground active compound and additives gives an emulsion concentrate which, by dilution with water, affords emulsions of the desired concentration.

EXAMPLE F2

Solutions

| | a) | b) | c) | d) |
|---|---|---|---|---|
| Active compound | 80% | 10% | 5% | 95% |
| Ethylene glycol monomethyl ether | — | 20% | — | — |
| Polyethylene glycol (MW 400) | — | 70% | — | — |
| N-methylpyrrolid-2-one | 20% | — | — | — |
| Epoxidized coconut oil | — | — | 1% | — |
| Aliphatic hydrocarbon (boiling range: 160-190°) | — | — | 94% | 5% |

Mixing of finely ground active compound and additives gives a solution suitable for use in the form of microdrops.

EXAMPLE F3

Granules

| | a) | b) | c) | d) |
|---|---|---|---|---|
| Active compound | 5% | 10% | 8% | 21% |
| Kaolin | 94% | — | 79% | 54% |
| Finely divided silicic acid | 1% | — | 13% | 7% |
| Attapulgite | — | 90% | — | 18% |

The active compound is dissolved in dichloromethane, the solution is sprayed onto the mixture of carriers and the solvent is evaporated under reduced pressure.

EXAMPLE F4

Wettable Powder

| | a) | b) | c) |
|---|---|---|---|
| Active compound | 25% | 50% | 75% |
| Sodium lignosulphonate | 5% | 5% | — |
| Sodium lauryl sulphate | 3% | — | 5% |
| Sodium diisobutylnaphthalene sulphonate | — | 6% | 10% |
| Octylphenol polyethylene glycol ether (7-8 mol of EO) | — | 2% | — |
| Finely divided silicic acid | 5% | 10% | 10% |
| Kaolin | 62% | 27% | — |

Active compound and additives are mixed and the mixture is ground in a suitable mill. This gives wettable powders which can be diluted with water to give suspensions of the desired concentration.

EXAMPLE F5

Emulsifiable Concentrate

| | |
|---|---|
| Active compound | 10% |
| Octylphenol polyethylene glycol ether (4-5 mol of EO) | 3% |
| Calcium dodecylbenzenesulphonate | 3% |
| Castor oil polyethylene glycol ether (36 mol of EO) | 4% |
| Cyclohexanone | 30% |
| Xylene mixture | 50% |

Mixing of finely ground active compound and additives gives an emulsion concentrate which, by dilution with water, affords emulsions of the desired concentration.

EXAMPLE F6

Extruder Granules

| | |
|---|---|
| Active compound | 10% |
| Sodium lignosulphonate | 2% |
| Carboxymethylcellulose | 1% |
| Kaolin | 87% |

Active compound and additives are mixed, the mixture is ground, moistened with water, extruded and granulated, and the granules are dried in a stream of air.

EXAMPLE F7

Coated Granules

| | |
|---|---|
| Active compound | 3% |
| Polyethylene glycol (MW 200) | 3% |
| Kaolin | 94% |

In a mixer, the finely ground active compound is applied uniformly to the kaolin which has been moistened with polyethylene glycol. This gives dust-free coated granules.

EXAMPLE F8

Suspension Concentrate

| | |
|---|---|
| Active compound | 40% |
| Ethylene glycol | 10% |
| Nonylphenol polyethylene glycol ether (15 mol of EO) | 6% |
| Sodium lignosulphonate | 10% |
| Carboxymethylcellulose | 1% |
| Aqueous formaldehyde solution (37%) | 0.2% |
| Aqueous silicone oil emulsion (75%) | 0.8% |
| Water | 32% |

Mixing of finely ground active compound and additives gives a suspension concentrate which, by dilution with water, affords suspensions of the desired concentration.

The compositions according to the invention may also comprise further solid or liquid adjuvants, such as stabilisers, e.g., vegetable oils or epoxidised vegetable oils (e.g., epoxidised coconut oil, rapeseed oil or soybean oil), antifoams, e.g. silicone oil, preservatives, viscosity regulators, binders and/or tackifiers as well as fertilisers or other active ingredients for obtaining special effects, e.g., acaricides, bactericides, fungicides, nematicides, molluscicides or selective herbicides.

The pesticidal composition according to the invention, particularly for use as a crop protection product, is prepared in the absence of adjuvants, e.g., by grinding, sieving and/or compressing the compound of formula (I) (as active ingredient) or mixture thereof, for example, to a certain particle size, and in the presence of at least one adjuvant, for example, by intimately mixing and/or grinding the compound of formula (I) (as active ingredient) or mixture thereof with the adjuvant(s). The invention relates likewise to those processes for the preparation of the pesticidal composition according to the invention and to the use of a compound of formula (I) in the preparation of the composition.

The invention relates also to the methods of application of the pesticidal and tank mix compositions, i.e., the methods of controlling pests of the mentioned type, such as spraying, atomising, dusting, coating, dressing, scattering or pouring, which are selected in accordance with the intended objectives and the prevailing circumstances, and to the use of the compositions for controlling pests of the mentioned type. Typical rates of concentration are from 0.1 to 1000 ppm, preferably from 0.1 to 500 ppm, of active ingredient. The rates of application per hectare are generally from 1 to 2000 g of active ingredient per hectare, especially from 10 to 1000 g/ha, preferably from 20 to 600 g/ha, most preferably from 20 to 100 g/ha.

A preferred method of application in the area of crop protection is application to the foliage of the plants (foliar application), the frequency and the rate of application being dependent upon the risk of infestation by the pest in question. However, the active ingredient can also penetrate the plants through the roots (systemic action) when the locus of the plants is impregnated with a liquid formulation or when the active ingredient is incorporated in solid form into the locus of the plants, for example, into the soil, e.g., in granular form (soil application). In the case of paddy rice crops, such granules may be applied in metered amounts to the flooded rice field.

The pesticidal and tank mix compositions are also suitable for protecting plant propagation material, e.g., seed, such as fruits, tubers or grains, or plant cuttings, against animal pests. The propagation material can be treated with the composition before planting: seed, for example, can be dressed before being sown. The active ingredients according to the invention can also be applied to grains (coating), either by impregnating the seeds in a liquid formulation or by coating them with a solid formulation. The composition can also be applied to the planting site when the propagation material is being planted, for example, to the seed furrow during sowing. The invention relates also to such methods of treating plant propagation material and to the plant propagation material so treated.

Further areas of use of the compounds according to the invention are the protection of stored goods and storerooms and the protection of raw materials, and also in the hygiene sector, especially the protection of domestic animals and productive livestock against pests of the mentioned type, more especially the protection of domestic animals, especially cats and dogs, from infestation by fleas, ticks and nematodes.

The following Examples serve to illustrate the invention. They do not limit the invention. Temperatures are given in degrees Celsius; mixing ratios of solvents are given in parts by volume.

PREPARATION EXAMPLES

In the following Examples, the preparation of avermectin B1 derivatives (mixtures of avermectin B1a and B1b derivative) is described. The B1b derivative generally represents about only from 5 to 10% by weight of the mixtures and, for that reason, usually only the bands of the B1a derivative can be detected in the NMR spectrum.

Since the compounds are in most cases in the form of mixtures of the avermectin B1a and B1b derivative, characterisation by means of the customary physical data such as melting point or refractive index is of little use. For that reason, the compounds are characterised by reference to the retention times determined in analysis by means of HPLC (high-resolution liquid chromatography). The term "B1a" in the physical data on the Preparation Examples refers to the main component, wherein $R_1$ is sec-butyl. "B1b" represents the secondary component, wherein $R_1$ is isopropyl. In the case of the compounds for which a retention time is given only for the B1a derivative, it is not possible to determine the retention time for the B1b component owing to the small proportion of B1b derivative. Allocation of the correct structures of the B1a and B1b components is carried out by mass spectrometry.

The following method is used for the HPLC analysis:

| HPLC gradient conditions | | | |
|---|---|---|---|
| solvent A: | 0.01% trifluoroacetic acid in $H_2O$ | | |
| solvent B: | 0.01% trifluoroacetic acid in $CH_3CN$ | | |
| time [min] | A [%] | B [%] | flow rate [µl/min] |
| 0 | 80 | 20 | 500 |
| 0.1 | 50 | 50 | 500 |
| 10 | 5 | 95 | 500 |
| 15 | 0 | 100 | 500 |

-continued

| HPLC gradient conditions | | | |
|---|---|---|---|
| 17 | 0 | 100 | 500 |
| 17.1 | 80 | 20 | 500 |
| 22 | 80 | 20 | 500 |

| | |
|---|---|
| column: | YMC-Pack ODS-AQ |
| column length: | 125 mm |
| column internal diameter: | 2 mm |
| temperature: | 40° C. |

The YMC-Pack ODS-AQ column used for chromatography of the compounds is produced by YMC, Alte Raesfelderstrasse 6, 46514 Schermbeck, Germany.

The abbreviations used in the physical data information have the following meanings:

LCMS: liquid chromatography mass spectrometry; $t_{RT}$: retention time in minutes; M+H: mass peak plus H; M+Na: mass peak plus Na. TBDMS in the Examples represents the radical —Si(CH$_3$)$_2$(tert-butyl). Mixing ratios of solvents are given in parts by volume. "Ether" is understood to mean diethyl ether.

EXAMPLE P.1

Preparation of 4'-(R)-4'-sulfamoyloxy-avermectin B1 monosaccharide of the Formula

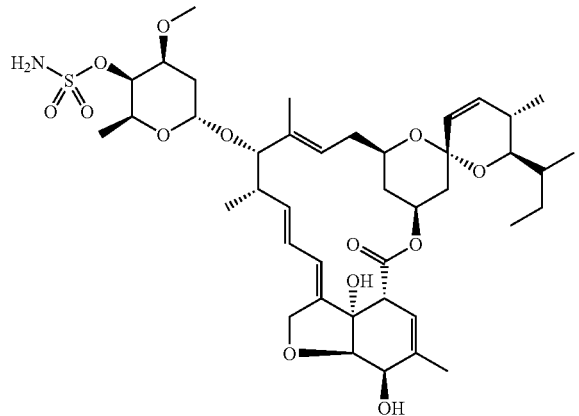

Preparation of sulfamoyl chloride (ClSO$_2$NH$_2$): 15.5 ml of formic acid are added dropwise at −10° C. to 35 ml of chlorosulfonyl isocyanate and the temperature is maintained below +10° C. by cooling with ice. At the end of the addition, stirring is continued at room temperature until the evolution of gas ceases. The mixture is taken up in benzene, filtered, and concentrated by evaporation in vacuo, yielding the desired sulfamoyl chloride.

Step A: 3.51 g of sulfamoyl chloride are added in portions at −10° C. to a solution of 15 g of 4'-epi-5-O-TBDMS-avermectin B$_1$ monosaccharide in 90 ml of dimethylacetamide under argon. The mixture is allowed to warm to room temperature and is stirred for a further hour. The mixture is poured onto saturated aqueous NaCl solution, extracted twice with tert-butyl methyl ether, dried over Na$_2$SO$_4$ and concentrated by evaporation, yielding the desired intermediate 5-O-TBDMS-4'-O-sulfamoyloxy-avermectin B$_1$ monosaccharide.

Step B: The crude product from Step A is dissolved in 75 ml of methanol. Then, at −5° C., 1.5 ml of methanesulfonic acid in 75 ml of methanol are added dropwise in the course of one hour. The mixture is allowed to warm to room temperature and is left to react for four hours. The solution is poured onto saturated aqueous NaHCO$_3$ solution, concentrated by evaporation in vacuo, and extracted twice with tert-butyl methyl ether. Washing with saturated aqueous NaCl solution, drying over Na$_2$SO$_4$ and concentration by evaporation yield the crude product. Flash column chromatography on silica gel in CH$_2$Cl$_2$/ethyl acetate (9:1) yields the desired product in the form of a colourless foam.

EXAMPLE P.2

Preparation of 4'-(S)-4'-isobutyroylaminosulfonyloxy-avermectin B1 monosaccharide of the Formula

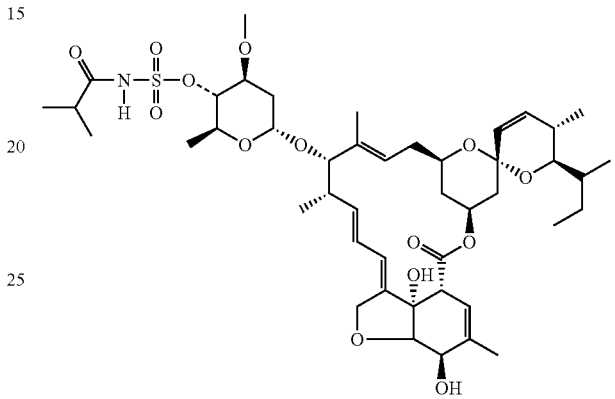

A mixture of 490 mg of 4'-sulfamoyloxy-5-O-t-butyldimethylsilyl-avermectin B1 monosaccharide, 0.26 ml of isobutyryl chloride and 0.41 ml of pyridine in 10 ml of dichloromethane is stirred overnight at 25° C. The mixture is filtered on silica gel and evaporated to dryness. The crude product is dissolved in 12 ml of tetrahydrofuran and a solution of 2.5 mL HF-Pyridine complex is added. The mixture is stirred overnight at room temperature. The mixture is poured onto a saturated solution of sodium hydrogen carbonate and extracted three times with ethyl acetate and the organic phases are combined and dried over Na$_2$SO$_4$. The desired product is isolated from the crude mixture by column chromatography on silicagel in hexane/ethyl acetate (1:1).

EXAMPLE P.3

Preparation of 4'-(S)-4'-dipropargylaminosulfonyloxy-avermectin B1 monosaccharide of the Formula

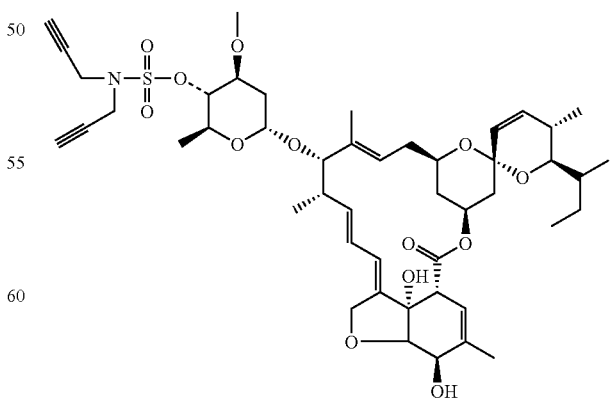

A mixture of 490 mg of 4'-sulfamoyloxy-avermectin B monosaccharide, 230 mg of potassium carbonate and 0.15 ml of propargyl bromide in 10 ml of acetonitrile is stirred at 50° C. for 3 hours. The solution is poured onto water, extracted with ethyl acetate and dried over $Na_2SO_4$. The desired product is isolated from the crude mixture by column chromatography on silica gel in hexane/ethyl acetate (1:4).

EXAMPLE P.4

Preparation of 4'-(S)-4'-Diallylaminosulfonyloxy-avermectin B1 monosaccharide

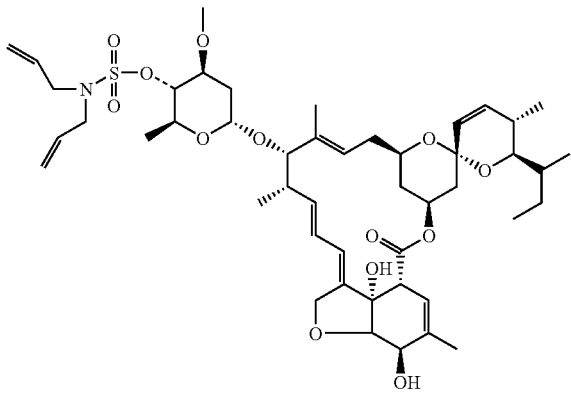

A mixture of 440 mg of 4'-sulfamoyloxy-avermectin B monosaccharide, 280 mg of potassium carbonate and 0.2 ml of propargyl bromide in 10 ml of acetonitrile is stirred at room temperature overnight and then refluxed for 2 hours. The solution is poured onto a saturated solution of sodium hydrogen-carbonate, extracted with ethyl acetate and dried over $Na_2SO_4$. The desired product is isolated from the crude mixture by column chromatography on silicagel in hexane/ethyl acetate (1:1).

HPLC characteristics of compounds are provided in Table A below.

BIOLOGICAL EXAMPLES

EXAMPLE B1

Action Against *Spodoptera littoralis*

Young soybean plants are sprayed with an aqueous emulsion spray mixture comprising 12.5 ppm of test compound and, after the spray-coating has dried, the plants are populated with 10 caterpillars of *Spodoptera littoralis* in the first stage and then placed in a plastics container. 3 days later, the percentage reduction in population and the percentage reduction in feeding damage (% activity) are determined by comparing the number of dead caterpillars and the feeding damage on the treated plants with that on untreated plants.

The compounds of formula (I) exhibit good activity in this test. In particular, compounds A.1, A.2, A.4, A.12, A.13 and A.16 are more than 80% effective.

EXAMPLE B2

Action Against *Spodoptera littoralis*, Systemic:

Maize seedlings are placed in the test solution. 6 days later, the leaves are cut off, placed on moist filter paper in a petri dish and infested with 12 to 15 *Spodoptera littoralis* larvae in the $L_1$ stage. 4 days later, the percentage reduction in population (% activity) is determined by comparing the number of dead caterpillars on treated plants with that on untreated plants.

The compounds of formula (I) exhibit good activity in this test. In particular, compounds A.1, A.2, A.4, A.12, A.13 and A.16 are more than 80% effective.

EXAMPLE B3

Action Against *Heliothis virescens*

30-35 eggs of *Heliothis virescens*, from 0 to 24 hours old, are placed on filter paper in a petri dish on a layer of artificial

TABLE A

Compounds of formula (Ia) or formula (Ib) wherein $R_1$ is sec-butyl (B1a) or isopropyl (B1b) and the bond between carbon atoms 22 and 23 is a double bond; and

| No. | Formula | $R_2$ | $R_3$ | retention time (min.) $B_{1a}$ | $B_{1b}$ |
|---|---|---|---|---|---|
| A.1 | (Ia) | H | H | 8.11 | — |
| A.2 | (Ia) | C(O)Me | H | 7.99 | 7.47 |
| A.3 | (Ia) | C(O)CH$_2$OCH$_3$ | H | 8.69 | — |
| A.4 | (Ia) | C(O)-i-C$_3$H$_7$ | H | 8.96 | 8.32 |
| A.5 | (Ia) | C(O)CH$_2$OC$_6$H$_5$ | H | 9.77 | — |
| A.6 | (Ia) | C(O)-i-C$_4$H$_9$ | H | 9.39 | 8.75 |
| A.7 | (Ia) | C(O)C$_6$H$_5$ | H | 9.28 | — |
| A.8 | (Ib) | Allyl | H | 5.35 | — |
| A.9 | (Ia) | Propargyl | propargyl | 10.83 | — |
| A.10 | (Ia) | Allyl | allyl | 11.63 | 10.93 |
| A.11 | (Ia) | —C(=O)C$_2$H$_5$ | H | 8.4 | — |
| A.12 | (Ia) | —CH$_2$OCH$_2$CH$_2$OCH$_3$ | —CH$_2$OCH$_2$CH$_2$OCH$_3$ | 10.57 | — |
| A.13 | (Ib) | H | H | 6.99 | — |
| A.14 | (Ib) | C(O)CH$_2$OCH$_3$ | H | 7.79 | — |
| A.15 | (Ib) | C(O)-i-C$_3$H$_7$ | H | 8.16 | — |
| A.16 | (Ib) | C(O)-i-C$_4$H$_9$ | H | 9.6 | — |
| A.17 | (Ib) | C(O)Me | H | 7.85 | — |
| A.18 | (Ib) | C(O)C$_6$H$_5$ | H | 9.45 | 10.66 |
| A.19 | (Ib) | Propargyl | propargyl | 9.89 | — |
| A.20 | (Ib) | Allyl | allyl | 6.72 | — | nutrient. 0.8 ml of the test solution is then pipetted onto the filter paper. Evaluation is made 6 days later. The percentage reduction in population (% activity) is determined by comparing the number of dead eggs and larvae on treated plants with that on untreated plants.

The compounds of formula (I) exhibit good activity in this test. In particular, compounds A.1, A.2, A.4, A.12, A.13 and A.16 are more than 80% effective.

EXAMPLE B4

Action Against *Plutella xylostella* Caterpillars

Young cabbage plants are sprayed with an aqueous emulsion spray mixture comprising 12.5 ppm of test compound. After the spray-coating has dried, the cabbage plants are populated with 10 caterpillars of *Plutella xylostella* in the first stage and placed in a plastics container. Evaluation is made 3 days later. The percentage reduction in population and the percentage reduction in feeding damage (% activity) are determined by comparing the number of dead caterpillars and the feeding damage on the treated plants with that on the untreated plants.

The compounds of formula (I) exhibit good activity in this test. In particular, compounds A.1, A.2, A.4, A.12, A.13 and A.16 are more than 80% effective.

EXAMPLE B5

Activity Against *Frankliniella occidentalis*

In Petri dishes, discs of the leaves of beans are placed onto agar and sprayed with test solution which comprises 12.5 ppm of active compound in a spraying chamber. The leaves are then populated with a mixed population of *Frankliniella occidentalis*. Evaluation is carried out after 10 days. The reduction in percent (% activity) is determined by comparing the population on the treated leaves with that of the untreated leaves.

The compounds of formula (I) exhibit good activity in this test. In particular, compounds A.1, A.2, A.4, A.12, A.13 and A.16 are more than 80% effective.

EXAMPLE B6

Action Against *Diabrotica balteata*

Maize seedlings are sprayed with an aqueous emulsion spray mixture comprising 12.5 ppm of the test compound and, after the spray-coating has dried, the maize seedlings are populated with 10 *Diabrotica balteata* larvae in the second stage and then placed in a plastics container. 6 days later, the percentage reduction in population (% activity) is determined by comparing the number of dead larvae on the treated plants with that on untreated plants.

The compounds of formula (I) exhibit good activity in this test. In particular, compounds A.1, A.2, A.4, A.12, A.13 and A.16 are more than 80% effective.

EXAMPLE B7

Action Against *Tetranychus urticae*

Young bean plants are populated with a mixed population of *Tetranychus urticae* and sprayed one day later with an aqueous emulsion spray mixture comprising 12.5 ppm of test compound. The plants are incubated for 6 days at 25° C. and subsequently evaluated. The percentage reduction in population (% activity) is determined by comparing the number of dead eggs, larvae and adults on the treated plants with that on untreated plants.

The compounds of formula (I) exhibit good activity in this test. In particular, compounds A.1, A.2, A.4, A.12, A.13 and A.16 are more than 80% effective.

What is claimed is:

1. A compound of formula (I)

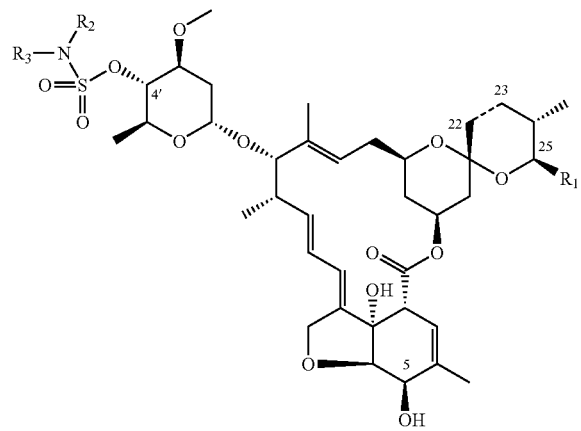

wherein the bond between carbon atoms 22 and 23 may be a single or a double bond;

$R_1$ is $C_1$-$C_{12}$alkyl, $C_3$-$C_8$cycloalkyl, or $C_2$-$C_{12}$alkenyl;

$R_2$ and $R_3$ are independently of each aryl or heteroaryl; wherein the aryl and heteroaryl radicals may be unsubstituted or mono- to penta-substituted;

wherein the substituents of the aryl and heteroaryl radicals defined under $R_2$ and $R_3$ are selected from the group consisting of OH; SH; —NH$_2$; CN; NO$_2$; halogen; $C_1$-$C_{12}$alkyl; halo-$C_1$-$C_2$alkyl; $C_1$-$C_{12}$alkenyl; $C_2$-$C_6$alkynyl; $C_3$-$C_8$cycloalkyl which is unsubstituted or substituted by from one to three methyl groups; norbornenyl; $C_3$-$C_8$cycloalkenyl that is unsubstituted or substituted by from one to three methyl groups; $C_3$-$C_8$halocycloalkyl; $C_1$-$C_{12}$alkoxy; $C_1$-$C_6$alkoxy-$C_1$-$C_6$alkyl; $C_1$-$C_6$alkoxy- $C_1$-$C_6$alkoxy; $C_1$-$C_6$alkoxy-$C_1$-$C_6$alkoxy- $C_1$-$C_6$alkyl; $C_2$-$C_{12}$alkenyloxy; $C_2$-$C_{12}$alkenyloxy- $C_1$-$C_6$alkoxy; $C_3$-$C_8$cycloalkoxy; $C_1$-$C_{12}$haloalkoxy; $C_1$-$C_{12}$alkylthio; $C_3$-$C_8$cycloalkylthio; $C_1$-$C_{12}$haloalkylthio; $C_1$-$C_{12}$alkylsulfinyl; $C_3$-$C_8$cycloalkylsulfinyl; $C_1$-$C_{12}$haloalkylsulfinyl; $C_3$-$C_8$halocycloalkylsulfinyl; $C_1$-$C_{12}$alkylsulfonyl; $C_3$-$C_8$cycloalkylsulfonyl; $C_1$-$C_{12}$haloalkylsulfonyl; $C_3$-$C_8$halocycloalkylsulfonyl; $C_2$-$C_8$alkenyl; $C_2$-$C_8$alkynyl; —NH($C_1$-$C_6$alkyl); —N($C_1$-$C_6$alkyl)$_2$; —C(=O)R$_4$; —NHC(=O)R$_5$; —P(=O)(OC$_1$-$C_6$alkyl)$_2$; aryl; heterocyclyl; aryloxy; and heterocyclyloxy; wherein the aryl, heterocyclyl, aryloxy and heterocyclyloxy radicals are unsubstituted or, depending upon the possibilities of substitution at the ring, mono- to penta-substituted by substituents selected from the group consisting of OH; halogen; CN; NO$_2$; $C_1$-$C_{12}$alkyl; $C_3$-$C_8$cycloalkyl; $C_1$-$C_{12}$haloalkyl; $C_1$-$C_{12}$alkoxy; $C_1$-$C_{12}$haloalkoxy; $C_1$-$C_{12}$alkylthio; $C_1$-$C_{12}$haloalkylthio; $C_1$-$C_{12}$alkylsulfinyl; $C_1$-$C_{12}$alkylsulfonyl; $C_1$-$C_6$alkoxy- $C_1$-$C_6$alkyl; dimethylamino- $C_1$-$C_6$alkoxy; $C_2$-$C_8$alkenyl;

$C_2$-$C_8$alkynyl; phenyl-$C_1$-$C_6$alkyl; phenoxy that is unsubstituted or substituted by from one to three substituents selected independently of one another from halogen, methoxy, trifluoromethyl and trifluoromethoxy; phenyl-$C_1$-$C_6$alkoxy that is unsubstituted or substituted in the aromatic ring by from one to three substituents selected independently of one another from halogen, methoxy, trifluoromethyl and trifluoromethoxy; phenyl-$C_2$-$C_6$alkenyl; phenyl-$C_2$-$C_6$alkynyl; methylenedioxy; —C(=O)$R_4$; —O—C(=O)$R_5$; —NHC(=O)$R_5$; —$NH_2$; —NH($C_1$-$C_{12}$alkyl); —N($C_1$-$C_{12}$alkyl)$_2$; $C_1$-$C_6$alkylthio; $C_1$-$C_6$alkylsulfinyl; $C_3$-$C_8$cycloalkylsulfinyl; $C_1$-$C_6$haloalkylsulfinyl; $C_3$-$C_8$halocycloalkylsulfinyl; $C_1$-$C_6$alkylsulfonyl; $C_3$-$C_8$cycloalkylsulfonyl; $C_1$-$C_6$haloalkylsulfonyl; and $C_3$-$C_8$halocycloalkylsulfonyl;

$R_4$ is H; OH; SH; $C_1$-$C_8$alkyl; $C_1$-$C_8$alkyl which is mono- to hepta-substituted by substituents selected from the group consisting of halogen, nitro, $C_1$-$C_8$alkoxy, aryloxy, OH, SH, —$NH_2$, —NH($C_1$-$C_{12}$alkyl) and —N($C_1$-$C_{12}$alkyl)$_2$; $C_1$-$C_8$alkoxy; halo-$C_1$-$C_8$alkoxy; $C_3$-$C_8$cycloalkyl; $C_3$-$C_8$cycloalkoxy; $C_2$-$C_8$alkenyl; $C_2$-$C_8$alkenyloxy; $C_2$-$C_8$alkynyl; $C_2$-$C_8$alkynyloxy; —$NH_2$; —NH($C_1$-$C_{12}$alkyl); —N($C_1$-$C_{12}$alkyl)$_2$; aryl; aryloxy; benzyl; benzyloxy; heterocyclyl; heterocyclyloxy; heterocyclylmethyl; or heterocyclylmethoxy; wherein the radicals aryl, aryloxy, benzyl, benzyloxy, heterocyclyl, heterocyclyloxy, heterocyclylmethyl and heterocyclylmethoxy are unsubstituted or, depending upon the possibilities of substitution at the ring, are substituted by from one to three substituents selected independently of one another from halogen, $C_1$-$C_{12}$alkyl, $C_1$-$C_{12}$haloalkyl, $C_1$-$C_{12}$alkoxy, $C_1$-$C_{12}$haloalkoxy, $C_1$-$C_6$alkoxy-$C_1$-$C_6$alkoxy, $C_1$-$C_{12}$alkylthio, $C_1$-$C_{12}$haloalkylthio, $C_1$-$C_{12}$alkylsulfinyl, $C_1$-$C_{12}$alkylsulfonyl, $C_2$-$C_8$alkenyloxy, $C_2$-$C_8$alkynyloxy, nitro, —$N_3$, and cyano;

$R_5$ is H, $C_1$-$C_{12}$alkyl, $C_1$-$C_6$alkoxy-$C_1$-$C_6$alkyl, $C_1$-$C_{12}$haloalkyl, $C_2$-$C_8$alkenyl, $C_2$-$C_8$alkynyl, aryl, heterocyclyl, benzyl, —$NH_2$, —NH($C_1$-$C_{12}$alkyl), —N($C_1$-$C_{12}$alkyl)$_2$, —NH-phenyl or —N($C_1$-$C_{12}$alkyl)-phenyl;

and, where applicable, to E/Z isomers, mixtures of E/Z isomers, diastereomers and/or tautomers, in each case in free form or in salt form.

2. A pesticidal composition comprising as active ingredient at least one compound of formula (I) as defined in claim 1, and at least one adjuvant.

3. A method of controlling pests, which comprises applying a composition as defined in claim 2 to the pests or to their habitat.

4. A process for the preparation of a composition comprising at least one adjuvant, as defined in claim 2, which comprises intimately mixing and/or grinding the active ingredient with the adjuvant(s).

5. A method for the protection of plant propagation material, which comprises treating the propagation material or the planting site of the propagation material with a pesticidal composition as defined in claim 2.

6. Plant propagation material treated in accordance with the method defined in claim 5.

7. A tank mix composition comprising a pesticidal composition defined in claim 2.

* * * * *